(12) United States Patent
Peyman et al.

(10) Patent No.: US 7,259,159 B2
(45) Date of Patent: Aug. 21, 2007

(54) GUANIDINO DERIVATIVES AS INHIBITORS OF CELL ADHESION

(75) Inventors: Anuschirwan Peyman, Kelkheim (DE); David Will, Kriftel (DE); Thomas R Gadek, Oakland, CA (US); Robert McDowell, San Francisco, CA (US); Jean Francois Gourvest, Claye Souilly (FR); Jean-Marie Ruxer, Issy les Moulineaux (FR); Jochen Knolle, Frankfurt am Main (DE)

(73) Assignees: Sanofi-Aventis Deutschland GmbH, Frankfurt am Main (DE); Genentech Inc., South San Francisco, CA (US)

( * ) Notice: Subject to any disclaimer, the term of this patent is extended or adjusted under 35 U.S.C. 154(b) by 0 days.

(21) Appl. No.: 10/343,173

(22) PCT Filed: Jul. 23, 2001

(86) PCT No.: PCT/EP01/08485

§ 371 (c)(1),
(2), (4) Date: Jan. 27, 2003

(87) PCT Pub. No.: WO02/10168

PCT Pub. Date: Feb. 7, 2002

(65) Prior Publication Data

US 2003/0203896 A1    Oct. 30, 2003

(30) Foreign Application Priority Data

Jul. 28, 2000    (EP) ................... 00116385

(51) Int. Cl.
| | |
|---|---|
| *C07D 471/04* | (2006.01) |
| *C07D 487/04* | (2006.01) |
| *C07D 473/16* | (2006.01) |
| *C07D 473/24* | (2006.01) |
| *C07D 473/28* | (2006.01) |
| *C07D 473/32* | (2006.01) |
| *C07D 473/34* | (2006.01) |
| *C07D 473/36* | (2006.01) |
| *C07D 473/40* | (2006.01) |
| *A61K 31/437* | (2006.01) |
| *A61K 31/519* | (2006.01) |

(52) U.S. Cl. .................. 514/218; 514/256; 514/263.2; 514/265.1; 514/269; 514/300; 514/303; 514/263.21; 540/553; 544/276; 544/277; 544/280; 544/331; 546/113; 546/118

(58) Field of Classification Search .............. 514/218, 514/256, 263.21, 265.1, 269, 300, 303, 263.2; 540/553; 544/276, 277, 280, 331, 264; 546/113, 546/118

See application file for complete search history.

(56) References Cited

FOREIGN PATENT DOCUMENTS

| EP | 0853084 A | 7/1998 |
|---|---|---|
| WO | WO99/32457 A | 7/1999 |
| WO | WO 00/31070 A | 6/2000 |

OTHER PUBLICATIONS

Diane M Biskobing, Expert Opinion on Investigational Drugs, 2003, vol. 12, No. 4, pp. 611-621.*

* cited by examiner

*Primary Examiner*—Mark L. Berch
*Assistant Examiner*—Susanna Moore
(74) *Attorney, Agent, or Firm*—James W. Bolcsak

(57) ABSTRACT

The present invention relates to acylguanidino derivatives of formula (I), in which $R^1$, $R^2$, $R^3$, A, B, X, Y and n have the meanings indicated in claim 1, their physiologically tolerable salts and their prodrugs. The compounds of the formula (I) are valuable pharmaceutically active compounds. They are vitronectin receptor antagonists and inhibitors of cell adhesion and bone resorption by osteoclasts. This renders them suitable, for example, for the therapy and prophylaxis of illness which are based on the interaction between vitronectin receptors and their ligands in cell-cell or cell-matrix interaction processes or which can be prevented, alleviated or cured by influencing such interactions. For example, they can be applied for treating and preventing osteoporosis, or for inhibiting undesired angiogenesis or proliferation of cells of the vascular smooth muscles. The invention furthermore relates to processes for the preparation of compounds of the formula (I), their use, in particular as pharmaceutical active ingredients, and pharmaceutical compositions comprising them

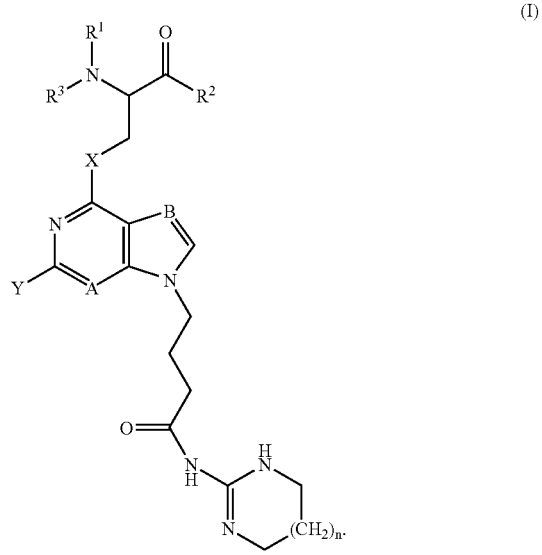

9 Claims, No Drawings

GUANIDINO DERIVATIVES AS INHIBITORS OF CELL ADHESION

This application is a 371 of PCT/EP01/08485 filed Jul. 23, 2001.

The present invention relates to acylguanidino derivatives of the formula I,

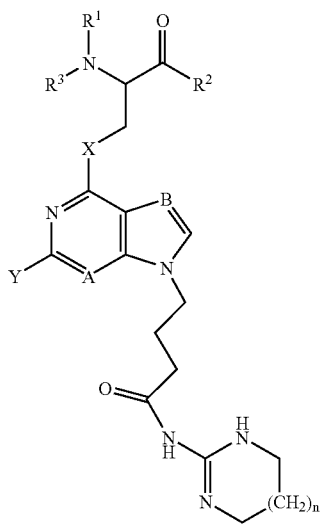

in which $R^1$, $R^2$, $R^3$, A, B, X, Y and n have the meanings indicated below, and their physiologically tolerable salts and prodrugs. The compounds of the formula I are valuable pharmaceutically active compounds. They are vitronectin receptor antagonists and inhibitors of cell adhesion and bone resorption by osteoclasts. This renders them suitable, for example, for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for treating and preventing osteoporosis, or for inhibiting undesired angiogenesis or proliferation of cells of the vascular smooth muscles. The invention furthermore relates to processes for the preparation of compounds of the formula I, their use, in particular as pharmaceutical active ingredients, and pharmaceutical compositions comprising them.

Human bones are subject to a constant dynamic renovation process comprising bone resorption and bone formation. These processes are controlled by types of cells specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry. 31 (1996) 211).

Activated osteoclasts are polynuclear cells having a diameter of up to 400 μm, which remove bone matrix. Activated osteoclasts become attached to the surface of the bone matrix and secrete proteolytic enzymes and acids into the "sealing zone", which is the space between the cell membrane of the osteoclasts and the bone matrix. The acidic conditions and the proteases cause the destruction of the bone. The compounds of the formula I inhibit bone resorption by osteoclasts.

There are studies which demonstrate that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth muscles, osteoclasts and tumor cells. The vitronectin receptor $\alpha_v\beta_3$, which is expressed on the osteoclast membrane, controls the process of attachment to the bones and bone resorption and thereby contributes to osteoporosis. $\alpha_v\beta_3$ in this case binds to bone matrix proteins such as osteopontin, bone sialoprotein and thrombospontin, which contain the tripeptide motif Arg-Gly-Asp (or RGD).

Horton and coworkers describe RGD peptides and an anti-vitronectin receptor antibody (23C6) which inhibit destruction of teeth by osteoclasts and the migration of osteoclasts (Horton et al., Exp. Cell. Res. 195 (1991) 368). Sato et al. characterize echistatin, an RGD peptide from snake venom, as a potent inhibitor of bone resorption in a tissue culture and as an inhibitor of osteoclast adhesion to the bones (J. Cell Biol. 111 (1990) 1713). Fischer et al. (Endocrinology 132 (1993) 1411) and Yamamoto et al. (Endocrinology 139 (1998) 1411) were able to demonstrate that echistatin also inhibits bone resorption in vivo in a rat model.

Vitronectin $\alpha_v\beta_3$ stimulates the migration of aorta vascular smooth muscle cells into the neointima, an event which in its final stage leads to arteriosclerosis and restenosis after angioplasty (Brown et al., Cardiovascular Res. 28 (1994) 1815). Yue et al. (Pharmacology Reviews and Communications 10 (1998) 9-18) describe the inhibition of neointima formation using an $\alpha_v\beta_3$ antagonist.

Brooks et al. (Cell 79 (1994) 1157) were able to demonstrate that antibodies against $\alpha_v\beta_3$ or $\alpha_v\beta_3$ antagonists cause shrinkage of tumors by inducing the apoptosis of blood vessel cells during angiogenesis. The vitronectin receptor ($\alpha_v\beta_3$) is further involved in the progression of a variety of other types of cancer. The receptor is for example overexpressed in malignant melanoma cells (Engleman et al., Annual Reports in Medicinal Chemistry. 31 (1996) 191). The melanoma invasiveness correlated with the overexpression (Stracke et al., Encylopedia of Cancer, volume 111, 1855, Academic Press, 1997; Hillis et al., Clinical Science 91 (1996) 639). Carron et al. (Cancer Res. 58 (1998) 1930) describe inhibition of tumor growth and inhibition of hypercalcemia of malignancy using an $\alpha_v\beta_3$ antagonist.

Friedlander et al. (Science 270 (1995) 1500) exhibit anti-$\alpha_v\beta_3$ antibodies or $\alpha_v\beta_3$ antagonists which inhibit the bFGF-induced angiogenesis processes in the eye of rats, a characteristic which can be used therapeutically in the treatment of retinopathies or in the treatment of psoriasis. Storgard et al. (J. Clin. Invest. 103 (1999) 47) describe the use of $\alpha_v\beta_3$ antagonists in the treatment of arthritic diseases.

Interference with the vitronectin receptor or interactions which it is participating thus offers the possibility of modifying different states of certain diseases which still desire therapy and prophylaxis by suitable pharmaceutical active ingredients.

EP-A-0 528 586 and EP-A-0 528 587 disclose aminoalkyl- or heterocyclyl-substituted phenylalanine derivatives, and WO 95/32710 discloses aryl derivatives as inhibitors of bone resorption by osteoclasts. In WO 95/28426 RGD peptides are described as inhibitors of bone resorption, angiogenesis and restenosis. International Patent Application WO 99/32457 discloses carbamic ester derivatives, and WO 99/37621 discloses sulfonamides which are vitronectin receptor antagonists. Further vitronectin receptor antagonists are disclosed in WO 98/08840 and WO 98/18461. Substituted purine derivatives as inhibitors of bone resorption are described in EP-A-0 853 084. Further investigations have shown that the compounds of the formula I are particularly strong inhibitors of the vitronectin receptor and of bone resorption by osteoclasts.

The present invention relates to compounds of the formula I,

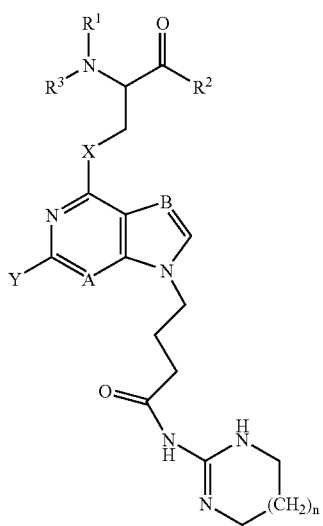

I in which
n is zero or one or two;
A is nitrogen or CH;
B is nitrogen or CH;
X is —$CH_2$—, —$NR^1$—, —O— or —S—;
Y is hydrogen, halogen, $NR^6R^{6'}$, ($C_1$-$C_{18}$)-alkyl, ($C_3$-$C_{14}$)-cycloalkyl-($C_0$-$C_8$)-alkyl, ($C_5$-$C_{14}$)-aryl-($C_0$-$C_8$)-alkyl, ($C_5$-$C_{14}$)-heteroaryl-($C_0$-$C_8$)-alkyl where aryl, heteroaryl cycloalkyl and alkyl can be substituted one, two or three times with fluorine, chlorine, bromine, cyano, $CF_3$, hydroxy, nitro, carboxyl, ($C_1$-$C_8$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl, ($C_1$-$C_6$)-alkylcarbonyl, ($C_1$-$C_6$)-alkylaminocarbonyl, ($C_1$-$C_6$)-alkoxy-($C_1$-$C_6$)-alkoxy-, ($C_5$-$C_{14}$)-aryl-($C_1$-$C_8$)-alkylcarbonyl, ($C_1$-$C_6$)-alkanoylamino, ($C_5$-$C_{14}$)-arylsulfonylamino, ($C_5$-$C_{14}$)-aryl-($C_1$-$C_8$)-alkylsulfonylamino, ($C_1$-$C_6$)-alkylsulfonylamino, ($C_1$-$C_6$)-alkylamino, di-(($C_1$-$C_6$)-alkyl)amino, ($C_1$-$C_6$)-alkylsulfonyl, ($C_1$-$C_6$)-alkylaminosulfonyl, ($C_5$-$C_{14}$)-aryl-($C_1$-$C_8$)-alkylaminosulfonyl, ($C_5$-$C_{14}$)-heteroaryl-($C_1$-$C_8$)-alkylaminosulfonyl, ($C_5$-$C_{14}$)-aryl-($C_1$-$C_8$)-alkylsulfonyl, ($C_5$-$C_{14}$)-heteroaryl-($C_1$-$C_8$)-alkylsulfonyl, ($C_5$-$C_{14}$)-aryl, or ($C_5$-$C_{14}$)-heteroaryl;
$R^1$ is hydrogen or ($C_1$-$C_4$)-alkyl;
$R^2$ is hydroxy, amino, ($C_1$-$C_6$)-alkyl-CO—O—($C_1$-$C_4$)-alkoxy, ($C_1$-$C_6$)-alkoxy, ($C_3$-$C_{16}$)-cycloalkyloxy, ($C_3$-$C_{16}$)-cycloalkyl-CO—O—($C_1$-$C_4$)-alkoxy, ($C_5$-$C_{14}$)-aryl-CO—O—($C_1$-$C_4$)-alkoxy where aryl, alkyl, alkoxy, cycloalkyloxy and cycloalkyl can be substituted by one, two or three radicals from the group consisting of hydroxyl, halogen, oxo, CN, ($C_1$-$C_4$)-alkyl-CO, ($C_1$-$C_4$)-alkyl-CO—NH, ($C_1$-$C_4$)-alkyl-NH—CO—, COOH, ($C_1$-$C_4$)-alkyl, ($C_1$-$C_4$)-alkoxy, ($C_1$-$C_4$)-alkyl-S(O)$_2$ and $NR^6R^{6'}$, or $R^2$ is an amino acid, bonded to C=O through its amino group, wherein natural amino acids are preferred; $R^3$ is $R^4$, $R^4C(O)R^5$, $R^4OC(O)R^5$, $R^4(O)_2R^5$, $R^4N(R^1)C(O)R^5$, $R^4N(R^1)S(O)_2R^5$; $R^4$ is ($C_1$-$C_{18}$)-alkyl, ($C_3$-$C_{14}$)-cycloalkyl-($C_0$-$C_8$)-alkyl, ($C_5$-$C_{14}$)-aryl-($C_0$-$C_8$)-alkyl, ($C_5$-$C_{14}$)-heteroaryl-($C_0$-$C_8$)-alkyl, where aryl, heteroaryl, cycloalkyl and alkyl can be substituted one, two or three times with fluorine, chlorine, bromine, cyano, $CF_3$, nitro, hydroxy, carboxyl, ($C_1$-$C_8$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl, ($C_1$-$C_6$)-alkylcarbonyl, ($C_1$-$C_6$)-alkylaminocarbonyl, ($C_1$-$C_6$)-alkoxy-($C_1$-$C_6$)-alkoxy-, ($C_5$-$C_{14}$)-aryl-($C_1$-$C_8$)-alkylcarbonyl, ($C_1$-$C_6$)-alkanoylamino, ($C_5$-$C_{14}$)-arylsulfonylamino, ($C_1$-$C_6$)-alkylsulfonylamino, ($C_1$-$C_6$)-alkylamino, di-(($C_1$-$C_6$)-alkyl)amino, ($C_1$-$C_6$)-alkylsulfonyl, ($C_1$-$C_6$)-alkylaminosulfonyl, ($C_5$-$C_{14}$)-aryl-($C_1$-$C_8$)-alkylaminosulfonyl, ($C_5$-$C_{14}$)-aryl-($C_1$-$C_8$)-alkylsulfonyl, ($C_5$-$C_{14}$)-aryl, ($C_5$-$C_{14}$)-heteroaryl;
$R^5$ is ($C_1$-$C_4$)-alkylene or a direct bond;
$R^6$ and $R^{6'}$ are independently of each other hydrogen, ($C_1$-$C_8$)-alkyl, ($C_3$-$C_{14}$)-cycloalkyl, ($C_3$-$C_{14}$)-cycloalkyl-($C_1$-$C_8$)-alkyl, ($C_5$-$C_{14}$)-aryl, ($C_5$-$C_{14}$)-aryl-($C_1$-$C_8$)-alkyl, in which, in the aryl moiety, one, two, three, four, or five ring carbon atoms can be replaced by heteroatoms such as N, O, S, or $R^6$ and $R^{6'}$, together with the atom connecting them form a ring system, in particular a 4- to 8-membered ring system, which can optionally also contain additional, in particular one, two or three additional, ring heteroatoms from the group consisting of N, O, S and which can be saturated or unsaturated;
in all their stereoisomeric forms and mixtures thereof in all ratios, and their physiologically tolerable salts and their prodrugs.

All radicals which can occur several times in the compounds of the formula I, for example the radicals $R^1$, can each independently of one another have the meanings indicated and can be identical or different.

The alkyl radicals occurring in the substituents can be straight-chain or branched, saturated or mono- or polyunsaturated. This also applies if they carry substituents or occur as substituents of other radicals, for example in alkoxy radicals, alkoxycarbonyl radicals or arylalkyl radicals. The same applies to alkylene radicals. Examples of alkyl residues containing from 1 to 18 carbon atoms are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Preferred alkyl radicals are methyl, ethyl, n-propyl, isopropyl, n-butyl, isobutyl, sec-butyl and tert-butyl. The bivalent radicals corresponding to the abovementioned monovalent radicals, for example methylene, ethylene, 1,3-propylene, 1,2-propylene (=1-methylethylene), 2,3-butylene (=1,2-dimethylethylene), 1,4-butylene, 1,6-hexylene, are examples of alkylene radicals.

Unsaturated alkyl residues can contain one or more, for example one, two or three, double bonds and/or triple bonds. Of course, an unsaturated alkyl residue has to have at least two carbon atoms. Examples of unsaturated alkyl radicals are alkenyl residues such as vinyl, 1-propenyl, allyl, butenyl, 3-methyl-2-butenyl or alkynyl radicals such as ethynyl, 1-propynyl or propargyl. Alkyl residues can also be unsaturated when they are substituted. Unsaturated alkylene residues, in particular alkenylene and alkynylene residues, can likewise be straight-chain or branched. Examples of alkenylene residues are vinylene or propenylene. Examples of alkynylene radicals are ethynylene or propynylene.

These statements relating to alkyl residues correspondingly apply to residues which may be regarded as divalent or polyvalent alkyl residues, for example the alkyl moiety in a substituted alkyl residue like hydroxy-alkyl-. The bonds via which the substituents in a substituted alkyl moiety are attached to their neighbouring group can be located in any desired positions.

Cycloalkyl residues can be monocyclic, bicyclic or tricyclic, i.e., they can be monocycloalkyl residues, bicycloalkyl residues and tricycloalkyl residues, provided they have a suitable number of carbon atoms and the parent hydrocarbons are stable. A bicyclic or tricyclic cycloalkyl residue has to have at least 4 carbon atoms. Preferably a bicyclic or tricyclic cycloalkyl residue has at least 5 carbon atoms, more preferably at least 6 carbon atoms, and up to the number of carbon atoms specified in the respective definition. Thus, $(C_3-C_{14})$-cycloalkyl comprises but is not limited to, for example, $(C_3-C_{14})$-monocycloalkyl, $(C_6-C_{14})$-bicycloalkyl and $(C_6-C_{14})$-tricycloalkyl, and $(C_3-C_{12})$-cycloalkyl comprises but is not limited to, for example, $(C_3-C_{12})$-monocycloalkyl, $(C_6-C_{12})$-bicycloalkyl and $(C_6-C_{12})$-tricycloalkyl.

Monocycloalkyl residues are, for example, cyclopropyl, cyclobutyl, cyclopentyl, cyclohexyl, cycloheptyl, cyclooctyl, cyclononyl, cyclodecyl, cycloundecyl, cyclododecyl or cyclotetradecyl which can also be substituted by, for example, $(C_1-C_4)$-alkyl. Examples of substituted cycloalkyl residues which may be mentioned are 4-methylcyclohexyl and 2,3-dimethylcyclopentyl.

Bicycloalkyl residues and tricycloalkyl residues can likewise be unsubstituted or substituted in any desired suitable position, for example by one or more oxo groups and/or one or more identical or different $(C_1-C_4)$-alkyl groups, for example methyl or isopropyl groups, preferably methyl groups. The bond via which the bicyclic or the tricyclic residue is bonded can be located in any desired position in the molecule; the residue can thus be bonded via a bridgehead atom or an atom in a bridge. The bond via which the residue is bonded can also be located in any desired stereochemical position, for example in an exo-position or an endo-position.

Examples of parent structures of bicyclic ring systems are norbornane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane). Examples of parent structures of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2. 1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane. A residue derived from adamantane can be 1-adamantyl or 2-adamantyl.

Halogen is, for example, fluorine, chlorine, bromine or iodine. $(C_5-C_{14})$-Aryl includes heterocyclic $(C_5-C_{14})$-aryl residues (=$(C_5-C_{14})$-heteroaryl residues) in which one or more of the 5 to 14 ring carbon atoms are replaced by heteroatoms such as nitrogen, oxygen or sulfur, and carbocyclic $(C_6-C_{14})$-aryl residues. Examples of carbocyclic $(C_6-C_{14})$-aryl residues are phenyl, naphthyl such as 1-naphthyl or 2-naphthyl, biphenylyl such as 2-biphenylyl, 3-biphenylyl or 4-biphenylyl, anthryl or fluorenyl, where $(C_6-C_{12})$-aryl residues, in particular 1-naphthyl, 2-naphthyl and phenyl, are preferred. If not stated otherwise, aryl residues, in particular phenyl residues, can be unsubstituted or substituted by one or more, preferably one, two or three, identical or different substituents. If not stated otherwise, substituted aryl residues can in particular be substituted by identical or different residues from the series consisting of $(C_1-C_8)$-alkyl, preferably $(C_1-C_6)$-alkyl, more preferably $(C_1-C_4)$-alkyl, $(C_1-C_8)$-alkoxy, preferably $(C_1-C_6)$-alkoxy, more peferably $(C_1-C_4)$-alkoxy, fluorine, chlorine and bromine, nitro, amino, trifluoromethyl, hydroxy, methylenedioxy, cyano, hydroxycarbonyl, aminocarbonyl, phenoxy, benzyl, benzyloxy, $(C_1-C_6)$-alkoxy-$(C_1-C_6)$-alkyl, $(C_1-C_6)$-alkoxycarbonyl, preferably $(C_1-C_4)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_8)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, preferably $(C_1-C_4)$-alkylamino, di-$((C_1-C_6)$-alkyl)amino, preferably di-$((C_1-C_4)$-alkyl)amino, $(C_1-C_6)$-alkylsulfonyl, $(C_1-C_6)$-alkylaminosulfonyl, $(C_5-C_{14})$-aryl-$(C_1-C_8)$-alkylaminosulfonyl, $(C_5-C_{14})$-aryl-$(C_1-C_8)$-alkylsulfonyl, $(C_5-C_{14})$-aryl including phenyl, $(C_5-C_{14})$-heteroaryl including tetrazolyl, $(R^9O)_2P(O)$— and $(R^9O)_2P(O)$—O— where $R^9$ is hydrogen, $(C_1-C_{10})$-alkyl, $(C_6-C_{14})$-aryl or $(C_6-C_{14})$-aryl-$(C_1-C_8)$-alkyl. A subgroup of substituents that can be present in aryl residues is formed by $(C_1-C_8)$-alkyl, in particular $(C_1-C_4)$-alkyl, $(C_1-C_8)$-alkoxy, in particular $(C_1-C_4)$-alkoxy, fluorine, chlorine and bromine, nitro, amino, $(C_1-C_4)$-alkylamino, di-$((C_1-C_4)$-alkyl)amino, trifluoromethyl, hydroxy, methylenedioxy, cyano, hydroxycarbonyl, aminocarbonyl, $(C_1-C_4)$-alkoxycarbonyl, phenyl, phenoxy, benzyl, benzyloxy, tetrazolyl, $(R^9O)_2P(O)$— and $(R^9O)_2P(O)$—O— where $R^9$ is hydrogen, $(C_1-C_{10})$-alkyl, $(C_6-C_{14})$-aryl or $(C_6-C_{14})$-aryl-$(C_1-C_8)$-alkyl. Usually only up to two nitro groups can be present in the compounds of the formula I, and similarly all other groups, substituents or heteroatoms mentioned in the definition of the compounds of the formula I can only be present in the compounds of the formula I in such positions and in such numbers and in such combinations that the resulting molecule is stable and does not exhibit characteristics that are not desired for the intended use.

In monosubstituted phenyl residues the substituent can be located in the 2-position, the 3-position or the 4-position, the 3-position and the 4-position being preferred. If phenyl is disubstituted, the substituents can be in 2,3-position, 2,4-position, 2,5-position, 2,6-position, 3,4-position or 3,5-position. Preferably in disubstituted phenyl residues the two substituents are located in 3,4-position relative to the linkage site. In trisubstituted phenyl residues, the substituents can be in 2,3,4-position, 2,3,5-position, 2,3,6-position, 2,4,5-position, 2,4,6-position or 3,4,5-position. Similarly, naphthyl residues and other aryl residues can be substituted in any desired position, for example a 1-naphthyl residue in the 2-, 3-, 4-, 5-, 6-, 7- and 8-position, a 2-naphthyl residue in the 1-, 3-, 4-, 5-, 6-, 7- and 8-position.

Beside carbocyclic systems, $(C_5-C_{14})$-aryl groups can also be monocyclic or polycyclic, for example monocyclic, bicyclic or tricyclic, aromatic ring systems in which 1, 2, 3, 4 or 5 ring carbon atoms are replaced by heteroatoms, in particular by identical or different heteroatoms from the series consisting of nitrogen, oxygen and sulfur. Examples of heterocyclic ($C_5$-$C_{14}$)-aryl groups and ($C_5$-$C_{14}$)-heteroaryl groups are pyridyl like 2-pyridyl, 3-pyridyl and 4-pyridyl, pyrrolyl like 2-pyrrolyl and 3-pyrrolyl, furyl like 2-furyl and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or benzo-fused, cyclopenta-fused, cyclohexa-fused or cyclohepta-fused derivatives of these residues. The heterocyclic systems can be substituted in any suitable position by the substituents listed above with respect to carbocyclic aryl systems.

In the series of heteroaryl groups, monocyclic or bicyclic aromatic ring systems which have 1, 2 or 3 ring heteroatoms, in particular 1 or 2 ring heteroatoms, from the series consisting of nitrogen, oxygen and sulfur and which can be unsubstituted or substituted by 1, 2 or 3 substituents from the series consisting of ($C_1$-$C_6$)-alkyl, ($C_1$-$C_6$)-alkoxy, fluorine, chlorine, nitro, amino, trifluoromethyl, hydroxy, ($C_1$-$C_4$)-alkoxycarbonyl, phenyl, phenoxy, benzyloxy and benzyl, are preferred. Particularly preferred here are monocyclic or bicyclic aromatic 5-membered to 10-membered ring systems having 1, 2 or 3 ring heteroatoms, in particular having 1 or 2 ring heteroatoms, from the series consisting of nitrogen, oxygen and sulfur which can be substituted by 1 to 2 substituents from the series consisting of ($C_1$-$C_4$)-alkyl, ($C_1$-$C_4$)-alkoxy, phenyl, phenoxy, benzyl and benzyloxy. More particularly preferred are 5-membered or 6-membered monocyclic heteroaryl groups and 9-membered or 10-membered bicyclic heteroaryl groups containing 1 or 2, in particular 1, ring heteroatom from the series consisting of nitrogen, oxygen and sulfur which are unsubstituted or substituted as described before.

A subgroup of aryl groups is formed by residues of six-membered monocyclic aromatic ring systems containing 0, 1, 2, 3, or 4 ring nitrogen atoms which are either unsubstituted or substituted as indicated above, in particular unsubstituted or substituted with fluorine, chlorine, bromine, cyano, $CF_3$, nitro, carboxyl, ($C_1$-$C_6$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl, ($C_1$-$C_6$)-alkylcarbonyl, ($C_1$-$C_6$)-alkylaminocarbonyl, ($C_1$-$C_6$)-alkoxy-($C_1$-$C_6$)-alkoxy-, ($C_5$-$C_{14}$)-aryl-($C_1$-$C_8$)-alkylcarbonyl, ($C_1$-$C_6$)-alkanoylamino, ($C_5$-$C_{14}$)-arylsulfonylamino, ($C_1$-$C_6$)-alkylsulfonylamino, ($C_1$-$C_6$)-alkylamino, di-(($C_1$-$C_6$)-alkyl)amino, ($C_1$-$C_6$)-alkylsulfonyl, ($C_1$-$C_6$)-alkylaminosulfonyl, ($C_5$-$C_{14}$)-aryl-($C_1$-$C_8$)-alkylaminosulfonyl, ($C_5$-$C_{14}$)-aryl-($C_1$-$C_8$)-alkylsulfonyl, ($C_5$-$C_{14}$)-aryl, or ($C_5$-$C_{14}$)-heteroaryl.

The above statements relating to aryl residues also correspondingly apply to the aryl moiety in groups like, for example, aryl-alkyl-. Examples of aryl-alkyl-residues which can also carry in the aryl moiety the substituents listed above, are benzyl, 1-phenylethyl or 2-phenylethyl.

In addition to the above-mentioned heteroaryl groups, as examples of saturated and unsaturated heterocyclic ring systems, including 4-membered to 8-membered ring systems, from which heterocyclic residues may be derived if they are in line with the definition of the respective group, there may be mentioned azetidine, tetrahydropyran, 1,4-dioxacyclohexane, morpholine, thiomorpholine, piperazine, piperidine, pyrrolidine, dihydroisoxazole, tetrahydroisoxazole, 1,3-dioxolane, 1,2-dithiolane, 2,3-dihydrofuran, 2,5-dihydrofuran, tetrahydrofuran, 2,3-dihydrothiophene, 2,5-dihydrothiophene, tetrahydrothiophene, 2-imidazoline, 3-imidazoline, 4-imidazoline, imidazolidine, 2-oxazoline, 3-oxazoline, 4-oxazoline, oxazolidine, 2-thiazoline, 3-thiazoline, 4-thiazoline, thiazolidine, 2H-thiapyran, 2H-pyran, 4H-pyran. A 4- to 8-membered ring system representing $R^6$ and $R^{6'}$ together with the nitrogen atom connecting them can contain 4, 5, 6, 7 or 8 ring members and preferably is morpholine, thiomorpholine, piperazine, piperidine or pyrrolidine.

Amino acids (amino carboxylic acids) representing $R^2$ are carboxylic acids containing one or several amino groups within the same molecule. They are bound to the C=O group in formula I carrying the group $R^2$ via an amino group with formation of an amide bond. An amino acid can be, for example, an α-amino acid in which an amino group and a carboxyl group are bound to the same carbon atom the position of which is called the α-position, or a β-amino acid. A preferred group of amino acid is formed by α-amino acids, in particular an L-α-amino acids. A preferred group of amino acids is further formed by natural amino acids of which proteins of living organisms are assembled and for which corresponding nucleic acids are coding, in particular natural L-α-amino acids. Especially preferred amino acids are alanine, valine, leucine, isoleucine, proline, tryptophane, phenylalanine, methionine, glycine, serine, tyrosine, threonine, cysteine, asparagine, glutamine, aspartic acid, glutamic acid, lysine, arginine, histidine, in particular the L-isomers. Functional groups in amino acids can be present in the form of derivatives. For example, a carboxylic acid group in an amino acid can be present as an ester such as an ($C_1$-$C_4$)-alkyl ester, or as an amide.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of race mates, or of mixtures of diastereomers. The present invention relates to both pure enantiomers and mixtures of enantiomers as well as to pure diastereomers and mixtures of diastereomers. The invention comprises mixtures of two or of more than two stereoisomers of the formula I, and it comprises all ratios of stereoisomers in the mixtures. Compounds of the formula I containing respective structural units can also be present as E isomers or Z isomers (or trans isomers or cis isomers). The invention relates to both pure E isomers, pure Z isomers, pure cis isomers, pure trans isomers and to E/Z mixtures and cis/trans mixtures in all ratios. The invention also comprises all tautomeric forms of the compounds of the formula I. Diastereomers, including E/Z isomers, can be separated into the individual isomers, for example, by chromatography. Racemates can be separated into the two enantiomers by customary methods, for example, by chromatography on chiral phases or by resolution, for example by crystallization of diastereomeric salts obtained with optically active acids or bases. Stereochemically unifom compounds of the formula I can also be obtained by employing stereochemically uniform starting materials or by using stereoselective reactions.

Physiologically tolerable salts of the compounds of the formula I are nontoxic salts that are physiologically acceptable, in particular pharmaceutically utilizable salts. Such salts of compounds of the formula I containing acidic groups, for example carboxyl, are, for example, alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine. Basic groups in the compounds of the formula I can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which simultaneously contain a basic group and an acidic group, for example a carboxyl group in addition to basic nitrogen atoms, can be present as zwitterions (or betaines or inner salts) which are likewise included by the present invention.

Salts of compounds of the formula I can be obtained by customary methods known to those skilled in the art, for example by combining a compound of the formula I with an inorganic or organic acid or base in a solvent or diluent, or from other salts by cation exchange or anion exchange. A subject of the present invention are also all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I like esters, prodrugs and other physiologically tolerable derivatives, as well as active metabolites of the compounds of the formula I. The invention relates in particular to prodrugs of the compounds of the formula I which can be converted into compounds of the formula I under physiological conditions. Suitable prodrugs for the compounds of the formula I, i.e. chemically modified derivatives of the compounds of the formula I having properties which are improved in a desired manner, are known to those skilled in the art. More detailed information relating to prodrugs and their preparation is found, for example, in Fleisher et al., Advanced Drug Delivery Reviews 19 (1996)115; Design of Prodrugs, H. Bundgaard (ed.), Elsevier, 1985; or H. Bundgaard, Drugs of the Future 16 (1991) 443; which are all incorporated herein by reference. Suitable prodrugs for the compounds of the formula I are especially ester prodrugs and amide prodrugs of carboxylic acid groups, in particular of a COOH group representing $COR^2$, for example alkyl esters, and also acyl prodrugs and carbamate prodrugs of acylatable nitrogen-containing groups such as amino groups or the guanidine group. In the acyl prodrugs or carbamate prodrugs, one or more, for example one or two, hydrogen atoms on nitrogen atoms in such groups are replaced by an acyl group or a carbamate group. Suitable acyl groups and carbamate groups for the acyl prodrugs and carbamate prodrugs are, for example, the groups $R^{10}$—C(O)— and $R^{11}$O—C(O)—, in which $R^{10}$ is hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl in which 1 to 5 carbon atoms can be replaced by heteroatoms such as nitrogen, oxygen or sulfur, or $(C_5-C_{14})$-aryl-$(C_1-C_8)$-alkyl- in which 1 to 5 carbon atoms in the aryl moiety can be replaced by heteroatoms such as nitrogen, oxygen or sulfur, and in which $R^{11}$ has the meanings indicated for $R^{10}$ with the exception of hydrogen.

A subgroup of preferred compounds of the formula I is formed by compounds wherein A is nitrogen and B is nitrogen, another subgroup by compounds wherein A is nitrogen and B is CH, another subgroup by compounds wherein A is CH and B is nitrogen, another subgroup by compounds wherein A is CH and B is CH, where all these compounds are comprised in all stereoisomeric forms and mixtures thereof in all ratios, and in the form of their physiologically tolerable salts and their prodrugs.

Within the scope of this invention n, X, Y, $R^1$, $R^2$, $R^3$, $R^4$, $R^5$ can adopt the afore defined meanings independently of each other.

n is preferably zero or one or two, more preferably zero or one, particularly preferably one.

X is preferably —$NR^1$— or —S—. A subgroup of particularly preferred compounds of the formula I is formed by compounds wherein X is —$NR^1$—, another subgroup by compounds wherein X is —S—.

Y is preferably hydrogen, $(C_1-C_6)$-alkyl, $(C_5-C_7)$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl in which aryl, heteroaryl, cycloalkyl and alkyl can be substituted one, two or three times with fluorine, chlorine, bromine, hydroxy, cyano, $CF_3$, nitro, $(C_1-C_4)$-alkyl, $(C_5-C_{14})$-aryl, $(C_5-C_{14})$-heteroaryl. More preferably Y is hydrogen, $(C_1-C_6)$-alkylor $(C_5-C_{14})$-aryl where aryl and alkyl can be substituted one or two times with fluorine, chlorine, bromine, hydroxy, $CF_3$, $(C_1-C_4)$-alkyl. Particularly preferably Y is hydrogen or $(C_1-C_3)$-alkyl.

$R^1$ is preferably hydrogen or methyl, more preferably hydrogen.

$R^2$ is preferably hydroxy, $(C_1-C_6)$-alkyl-CO—O—$(C_1-C_4)$-alkoxy, $(C_1-C_6)$-alkoxy, more preferably hydroxy or $(C_1-C_4)$-alkoxy.

$R^3$ is preferably $R^4$, $R^4C(O)R^5$, $ROC(O)R^5$, $R^4S(O)_2R^4$, $R^4N(R^1)C(O)R^5$, or $R^4N(R^1)S(O)_2R^5$, more preferably $R^4$, $R^4OC(O)R^5$, or $R^4S(O)_2R^5$, particularly preferably $R^4OC(O)R^4$ or $R^4S(O)_2R^5$.

$R^4$ is preferably $(C_1-C_{18})$-alkyl, $(C_3-C_{14})$-cycloalkyl-$(C_0-C_8)$-alkyl, $(C_5-C_{14})$-aryl-$(C_0-C_8)$-alkyl, $(C_5-C_{14})$-heteroaryl-$(C_0-C_8)$-alkyl, in which aryl, heteroaryl, cycloalkyl and alkyl can be substituted one, two or three times with fluorine, chlorine, bromine, hydroxy, cyano, $CF_3$, $(C_1-C_4)$-alkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkylaminocarbonyl, $(C_1-C_4)$-alkylamino, di-$((C_1-C_4)$-alkyl)amino, $(C_1-C_4)$-alkylsulfonyl, $(C_1-C_4)$-alkylaminosulfonyl, $(C_5-C_{14})$-aryl-$(C_1-C_8)$-alkylaminosulfonyl, $(C_5-C_{14})$-aryl-$(C_1-C_8)$-alkylsulfonyl, $(C_5-C_{14})$-aryl, $(C_5-C_{14})$-heteroaryl. More preferably $R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one, two or three times with fluorine, chlorine, bromine, hydroxy, $CF_3$, $(C_1-C_4)$-alkyl, $(C_1-C_4)$-alkoxy, $(C_1-C_4)$-alkylcarbonyl, $(C_5-C_{14})$-aryl, $(C_5-C_{14})$-heteroaryl. Particularly preferably $R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one or two times with fluorine, chlorine, bromine, hydroxy, $CF_3$, $(C_1-C_4)$-alkyl.

$R^5$ preferably is a direct bond.

The invention further includes a preferred compound of the formula I wherein n is zero or one or two;

X is —$NR^1$— or —S—;

Y is hydrogen, $(C_1-C_6)$-alkyl, $(C_5-C_7)$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl in which aryl, heteroaryl, cycloalkyl and alkyl can be substituted one, two or three times with fluorine, chlorine, bromine, hydroxy, cyano, $CF_3$, nitro, $(C_1-C_4)$-alkyl, $(C_5-C_{14})$-aryl, $(C_5-C_{14})$-heteroaryl;
$R^1$ is hydrogen or methyl;
$R^2$ is hydroxy, $(C_1-C_6)$-alkyl-CO—O—$(C_1-C_4)$-alkoxy, $(C_1-C_6)$-alkoxy;
$R^3$ is $R^4$, $R^4C(O)R^5$, $R^4OC(O)R^5$, $R^5S(O)_2R^5$, $R^4N(R^1)C(O)R^5$, $R^4N(R^1)S(O)_2R^5$;
$R^4$ is $(C_1-C_{18})$-alkyl, $(C_3-C_{14})$-cycloalkyl-$(C_0-C_8)$-alkyl, $(C_5-C_{14})$-aryl-$(C_0-C_8)$-alkyl, $(C_5-C_{14})$-heteroaryl-$(C_0-C_8)$-alkyl in which aryl, heteroaryl, cycloalkyl and alkyl can be substituted one, two or three times with fluorine, chlorine, bromine, hydroxy, cyano, $CF_3$, $(C_1-C_4)$-alkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkylaminocarbonyl, $(C_1-C_4)$-alkylamino, di-($(C_1-C_4)$-alkyl)amino, $(C_1-C_4)$-alkylsulfonyl, $(C_1-C_4)$-alkylaminosulfonyl, $(C_5-C_{14})$-aryl-$(C_1-C_8)$-alkylaminosulfonyl, $(C_5-C_{14})$-aryl-$(C_1-C_8)$-alkylsulfonyl, $(C_5-C_{14})$-aryl, $(C_5-C_{14})$-heteroaryl;
$R^5$ is a direct bond;
in all their stereoisomeric forms and mixtures thereof in all ratios, and their physiologically tolerable salts and their prodrugs.

The invention further includes a preferred compound of the formula I wherein
n is zero or one;
X is —$NR^1$— or —S—;
Y is hydrogen, $(C_1-C_6)$-alkyl or $(C_5-C_{14})$-aryl where aryl and alkyl can be substituted one or two times with fluorine, chlorine, bromine, hydroxy, $CF_3$, $(C_1-C_4)$-alkyl;
$R^1$ is hydrogen or methyl;
$R^2$ is hydroxy or $(C_1-C_4)$-alkoxy;
$R^3$ is $R^4$, $R^4OC(O)R^5$, $R^4S(O)_2R^5$;
$R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one, two or three times with fluorine, chlorine, bromine, hydroxy, $CF_3$, $(C_1-C_4)$-alkyl, $(C_1-C_4)$-alkoxy, $(C_1-C_4)$-alkylcarbonyl, $(C_5-C_{14})$-aryl, $(C_5-C_{14})$-heteroaryl;
$R^5$ is a direct bond;
in all their stereoisomeric forms and mixtures thereof in all ratios, and their physiologically tolerable salts and their prodrugs.

The invention further includes a preferred compound of the formula I wherein
n is one;
X is —$NR^1$— or —S—;
Y is hydrogen or $(C_1-C_3)$-alkyl;
$R^1$ is hydrogen;
$R^2$ is hydroxy or $(C_1-C_4)$-alkoxy;
$R^3$ is $R^4$, $R^4OC(O)R^5$, $R^4S(O)_2R^5$;
$R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one or two times with fluorine, chlorine, bromine, hydroxy, $CF_3$, $(C_1-C_4)$-alkyl;
$R^5$ is a direct bond;
in all their stereoisomeric forms and mixtures thereof in all ratios, and their physiologically tolerable salts and their prodrugs.

Within this invention is further included a preferred compound of the formula I, wherein
n is one;
X is —$NR^1$—;
Y is hydrogen or $(C_1-C_3)$-alkyl;
$R^1$ is hydrogen;
$R^2$ is hydroxy or $(C_1-C_4)$-alkoxy;
$R^3$ is $R^4OC(O)R^5$, $R^4S(O)_2R^5$;
$R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one or two times with fluorine, chlorine, bromine, hydroxy, $CF_3$, $(C_1-C_4)$-alkyl;
$R^5$ is a direct bond;
in all their stereoisomeric forms and mixtures thereof in all ratios, and their physiologically tolerable salts and their prodrugs.

Within this invention is further included a preferred compound of the formula I, wherein
n is one;
X is —S—;
Y is hydrogen or $(C_1-C_3)$-alkyl;
$R^1$ is hydrogen;
$R^2$ is hydroxy or $(C_1-C_4)$-alkoxy;
$R^3$ is $R^4OC(O)R^5$, $R^4S(O)_2R^5$;
$R^4$ is $(C_1-C_{10})$-alkyl, $(C_3-C_{14})$-cycloalkyl-$(C_0-C_3)$-alkyl, $(C_5-C_{14})$-aryl-$(C_0-C_3)$-alkyl, $(C_5-C_{14})$-heteroaryl-$(C_0-C_3)$-alkyl where aryl, heteroaryl, cycloalkyl and alkyl can be substituted one or two times with fluorine, chlorine, bromine, hydroxy, $CF_3$, $(C_1-C_4)$-alkyl;
$R^5$ is a direct bond;
in all their stereoisomeric forms and mixtures thereof in all ratios, and their physiologically tolerable salts and their prodrugs.

In case X is —$NR^1$—, —$CH_2$— or —O— the carbon atom of a compound of the formula I which is bound to the groups $R^2$—CO— and $R^1R^3N$— is preferably present in S configuration. In case X is —S— the carbon atom of a compound of the formula I which is bound to the groups $R^2$-CO— and $R^1R^3N$— is preferably present in R configuration.

The present invention also relates to processes for the preparation of the compounds of the formula I. The compounds can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step, in the form of precursors which are later converted into the desired functional groups, or to temporarily block functional groups by a protective group strategy adapted to the synthesis problem, which is known to those skilled in the art (Greene, Wuts, Protective Groups in Organic Synthesis, Wiley, 1991).

Thus the compounds of the formula I can be prepared, for example, by reacting a compound of the formula II

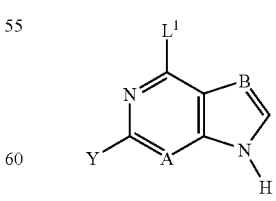

II wherein Y, A and B are defined as abovementioned and $L^1$ is a nucleophilically substitutable leaving group, e.g. halogen, preferably chlorine, with a compound of the formula III,

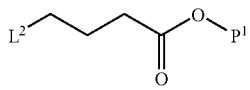

III wherein $L^2$ is a nucleophilically substitutable leaving group, preferably halogen like chlorine or bromine, and $P^1$ is a carboxylic acid protecting group (Greene, Wuts, Protective Groups in Organic Synthesis, Wiley, 1991), preferably methyl or ethyl or benzyl.

Compounds of the formula II in which A and B are nitrogen, such as 6-chloropurine, 2,6-dichloropurine or 2-amino-6-chloropurine, are commercially available or can be easily prepared by known methods. Compounds of the formula II in which A is nitrogen and B is CH can easily be prepared by methods known to those skilled in the art, for example in analogy to the synthesis of 4-chloro-2-methyl-7H-pyrrolo[2,3-d]pyrimidine (West and Beauchamp, J. Org. Chem. 26 (1961) 3809). Compounds of the formula II in which A is CH and B is CH, can easily be prepared by methods known to those skilled in the art, for example in analogy to the synthesis of 4-chloro-1H-pyrrolo[3,2-c]pyridine (Mahadevan and Rasmussen J. Heterocycl. Chem. 29 (1992) 359).

The reaction of a compound of the formula II with a compound of the formula III is preferably carried out in a suitable organic solvent, in particular DMF (dimethylformamide), NMP (N-methylpyrrolidone), THF (tetrahydrofuran), in the presence of a suitable base, in particular $K_2CO_3$. The reaction results in a compound of the formula IV,

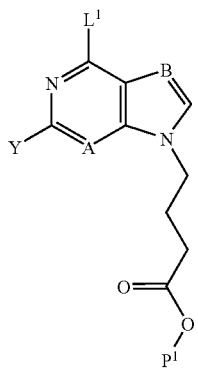

IV wherein $L^1$, $P^1$, Y, A, B are defined as abovementioned, which is further reacted with a compound of the formula V,

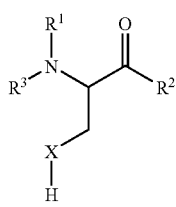

V wherein X, $R^1$, $R^2$, and $R^3$ are defined as abovementioned.

Alternatively the functional groups in the compounds of the formula II, III, IV, V can be present in the form of precursors or in the form of protected groups which can later be converted into the groups present in the compounds of the formula I. A protective group can be for example a tert-butoxy group.

The reaction of a compound of the formula IV with a compound of the formula V is preferably performed in a suitable organic solvent, in particular in DMF, NMP or THF, optionally in the presence of a suitable base such as triethylamine (TEA) or diisopropylethylamine (DIPEA), which reaction results in a compound of the formula VI,

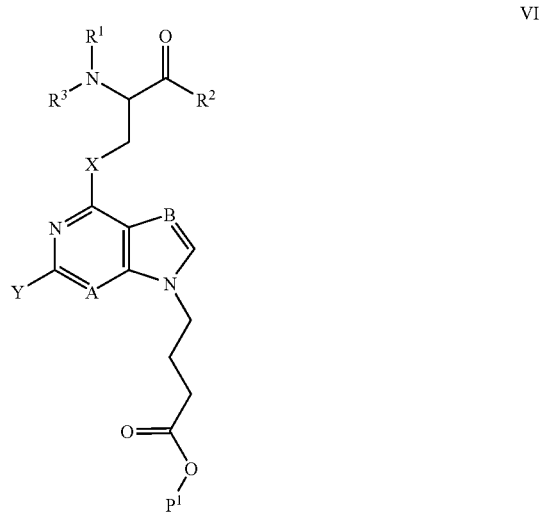

VI wherein X, $R^1$, $R^2$, $R^3$, Y, $P^1$, A, and B are defined as abovementioned.

Compounds of the formula VI are converted into compounds of the formula VII by methods known to those skilled in the art (Greene, Wuts, Protective Groups in Organic Synthesis, Wiley, 1991) by removal of the protecting group $P^1$ and optionally activating the resulting carboxylic acid unless $P^1$ means, for example, methyl, ethyl or benzyl in which cases the removal step may be omitted. In the compound of the formula VII

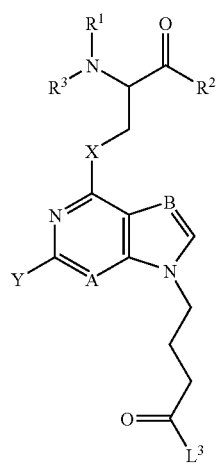

VII

X, $R^1$, $R^2$, $R^3$, Y, A, and B are defined as abovementioned and $L^3$ is a nucleophilically substitutable leaving group.

A compound of the formula VII, or a compound of the formula VI in case the removal of $P^1$ in a compound of the formula VI has been omitted, is reacted with a guanidine or guanidine derivative of the formula VII

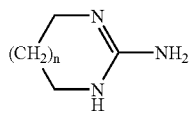

VIII which reaction results in a compound of the formula I. In the compounds of the formula VII n is defined as abovementioned.

The group $COL^3$ in the formula VII is preferably the carboxylic acid group COOH or an activated carboxylic acid derivative. $L^3$ can be, for example, hydroxyl, halogen, in particular chlorine or bromine, alkoxy, preferably methoxy or ethoxy, aryloxy, preferably phenoxy or pentafluorophenoxy, phenylthio, methylthio, 2-pyridylthio or a radical of a nitrogen heterocycle bonded via a nitrogen atom, in particutar of an azole, such as, for example, 1-imidazolyl. $L^3$ can also be, for example, $((C_1-C_4)$-alkyl)-CO—CO— or tolylsulfonyloxy, i.e. the activated acid derivative can be a mixed anhydride. In case $L^3$ is hydroxyl, i.e. if the guanidine of the formula VIII is reacted with a carboxylic acid, then the carboxylic acid is expediently first activated. The activation can be carried out, for example, with DCCl (dicyclohexylcarbodiimide) or with TOTU (O-((cyano(ethoxycarbonyl)-methylene)amino)-1,1,3,3-tetramethyluronium tetrafluoroborate) or HATU (7-azabenzotriazol-1-yl-N,N,N',N'-tetramethyluronium hexafluorophosphate) or other activating reagents customary in peptide chemistry. A number of suitable methods for the preparation of activated carboxylic acid derivatives are also indicated with details of source literature in J. March, Advanced Organic Chemistry, Third Edition, John Wiley & Sons, 1985, p. 350.

Beside the free guanidines of the formula VIII, guanidinium salts can also be employed in the reaction with the compounds of the formula VII, from which the free guanidines are then prepared in situ or in a separate step by means of a base. The reaction of an activated carboxylic acid derivative of the formula VII with the guanidine or a guanidine derivative of the formula VIII is preferably carried out in a manner known per se in a protic or aprotic polar, but inert, organic solvent. For example, in the reaction of the methyl esters ($L^3$=methoxy) or of the ethyl esters ($L^3$=ethoxy) with the guanidines, methanol, isopropanol, tert-butanol, dimethylformamide or tetrahydrofuran at temperatures from 0° C. up to the boiling temperature of these solvents have proven suitable. In other cases the reactions of compounds of the formula VII with guanidines are advantageously carried out in aprotic inert solvents such as dimethylformamide, tetrahydrofuran, dimethoxyethane or dioxane, if appropriate with addition of a base such as, for example, potassium tert-butoxide or sodium methoxide. However, water can also be used as a solvent in the reaction of compounds of the formula VII with guanidines, for example when using a base such as sodium hdyroxide. If $L^3$ is chlorine, the reaction is advantageously carried out with addition of an acid scavenger, for example of an added base or in the presence of excess guanidine (derivative) for binding the resulting hydrohalic acid. The reaction mixture is worked up and, if desired, the reaction product is then purified by the customary processes familiar to those skilled in the art.

Protective groups optionally still present in the obtained products are then removed by standard processes. For example tert-butyl ester groups are converted into the carboxylic acid groups by treatment with trifluoroacetic acid. Benzyl groups are removed by hydrogenation whereas fluorenylmethoxycarbonyl groups are removed by secondary amines. Further reactions, for example acylation reactions, can then be carried out by standard processes and, if appropriate, conversions into physiologically tolerable salts or prodrugs can be carried out by known processes.

The compounds of the formula I are valuable pharmacologically active compounds which are suitable, for example, for the therapy and prophylaxis of bone disorders, tumor diseases, cardiovascular disorders or inflammatory conditions. The compounds of the formula I and their physiologically tolerable salts and their prodrugs can be administered to animals, preferably to mammals, and in particular to humans as pharmaceuticals for therapy or prophylaxis. They can be administered on their own or in mixtures with one another or in the form of pharmaceutical compositions which permit enteral or parenteral administration and which, as active constituent, contain an efficacious dose of at least one compound of the formula I and/or its physiologically tolerable salts and/or its prodrugs in addition to a pharmaceutically acceptable carrier.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases and to methods for such therapy and prophylaxis. The present invention furthermore relates to pharmaceutical compositions (or pharmaceutical preparations) which contain an efficacious dose of at least one compound of the formula I and/or its physiologically tolerable salts and/or its prodrugs and a pharmaceutically acceptable carrier, i.e. one or more carrier substances (or excipients) and/or auxiliary substances (or additives).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions emulsions or tinctures, or in other ways, for example in the form of aerosols or nasal sprays.

The pharmaceutical compositions according to the invention are prepared in a manner known per se and familiar to those skilled in the art, one or more compound(s) of the formula I and/or its (their) physiologically tolerable salts and/or its (their) prodrugs being mixed with one or more pharmaceutically acceptable inert inorganic and/or organic carrier substances and/or additives and, if desired, one or more other pharmaceutically active compounds and being brought into a suitable administration form and dosage form that can be used in human or veterinary medicine. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical compositions normally is from about 0.2 mg to about 500 mg, preferably from about 1 mg to about 200 mg.

In addition to the active ingredients of the formula I and/or its physiologically tolerable salts and/or its prodrugs and carrier substances, the pharmaceutical compositions can contain additives such as, for example, fillers, disintegrants, binders, lubricants, wefting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteoclasts. The action of the compounds of the formula I can be demonstrated, for example, in an assay in which the inhibition of the binding of the isolated vitronectin receptor or of cells which contain the vitronectin receptor to a ligand of the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical composition, for example tablets, capsules or granules, or can be present in two or more separate pharmaceutical compositions which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical compositions which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically acceptable carrier. The above explanations on pharmaceutical compositions correspondingly apply to such pharmaceutical combination compositions.

Apart from use as inhibitors of bone resorption by osteoclasts, the compounds of the formula I and their physiologically tolerable salts and their prodrugs can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer (Academic Press), 1997. All the above statements relating to the use of the compounds of the formula I in combination with conventional osteoporosis therapy like, for example, possible modes of administration and pharmaceutical combination compositions, correspondingly apply to the use of the compounds of the formula I in combination with conventional cancer therapy.

When using the compounds of the formula I, the dose can vary within wide limits and, as is customary, is to be suited to the individual conditions in each individual case. It depends, for example, on the compound employed, on the nature and severity of the disease to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of the formula I can also be used as vehicles or carriers of other active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag which is incorporated herein by reference). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example by introduction of substituents or modification of functional groups.

EXAMPLES

The products were identified via mass spectra (MS) and/or NMR spectra. Compounds which were purified by chromatography using an acidic eluent containing, for example, acetic acid or trifluoroacetic acid, could still contain acid originating from the eluent when after elution the compound had been freeze dried depending on the applied conditions for freeze-drying. Compounds could also contain acid in case when within the last synthesis step an acid was used, for example when trifluoroacetic acid was employed to remove a tert-butyl protective group. Compounds containing an acid were obtained partially or completely in the form of a salt of the acid used, for example in the form of the acetic acid salt or trifluoroacetic acid salt.

| Abbreviations | |
|---|---|
| AcOH | acetic acid |
| DCM | dichloromethane |
| DMF | N,N-dimethylformamide |
| EE | ethyl acetate |
| MeOH | methanol |
| TFA | trifluoroacetic acid |
| THF | tetrahydrofuran |
| DIPEA | diisopropylethylamine |

Example 1

(2S)-2-Benzyloxycarbonylamino-3-{9-[3-(1,4,5,6-tetrahydro-pyrimidin-2-ylcarbamoyl)-propyl]-9H-purin-6-ylamino}-propionic acid

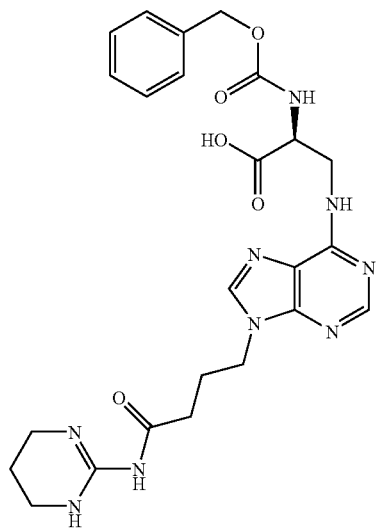

1a) 4-(6-Chloro-purin-9-yl)-butyric acid ethyl ester 25 g (0.162 mol) of 6-chloropurine was dissolved in 500 ml of dimethylformamide and 89.4 g (0.647 mol) of potassium carbonate was added to this solution. 23.4 ml (0.162 mol) of 4-bromobutyric acid ethyl ester was added dropwise over a period of 4 hours. The solution was stirred for 16 h at room temperature. The solvent was removed in vacuo, the residue was dissolved in EE and the solution was washed three times with water and once with saturated aqueous sodium chloride solution. The organic phase was dried with sodium sulfate, filtered and the solvent was removed in vacuo. The residue was chromatographed on silica gel eluting with DCM/EE (1/1). Yield: 28.7 g.

MS (ES$^+$): m/e=269/271 (M+H$^+$).

1b) 4-[6-((2S)-2-Benzyloxycarbonylamino-2-tert-butoxycarbonyl-ethylamino)-purin-9-yl]-butyric acid ethyl ester 1 g (3.72 mmol) of 4-(6-chloro-purin-9-yl)-butyric acid ethyl ester was dissolved in dimethylformamide (3 ml) and 2.6 ml (14.9 mmol) of N,N-diisopropylethylamine was added. 1.09 g (3.72 mmol) of (2S)-3-amino-2-benzyloxycarbonylamino-propionic acid tert-butyl ester and dimethylformamide (2 ml) were added. The reaction was stirred at 80° C. for 2 days. The solvent was removed in vacuo, the residue was dissolved in dichloromethane and the solution was washed three times with 10% aqueous citric acid solution and three times with water. The organic phase was dried with sodium sulfate, filtered and the solvent was removed in vacuo. Residual amounts of 4-(6-chloro-purin-9-yl)-butyric acid ethyl ester were removed as follows: the residue was dissolved in tetrahydrofuran and 2 g of a macroporous aminomethyl polystyrene resin was added. The suspension was heated at 60° C. for 5 hours, then stirred gently at room temperature for 16 hours. The resin was filtered off, washed with tetrahydrofuran, and the combined organic phase was dried in vacuo. Yield: 908 mg.

MS (ES$^+$): m/e=527 (M+H$^+$).

1c) (2S)-2-Benzyloxycarbonylamino-3-{9-[3-(1,4,5,6-tetrahydro-pyrimidin-2-ylcarbamoyl)-propyl]-9H-purin-6-ylamino}-propionic acid tert-butyl ester 200 mg (0.38 mmol) of 4-[6-((2S)-2-benzyloxycarbonylamino-2-tert-butoxycarbonyl-ethylamino)-purin-9-yl]-butyric acid ethyl ester was dissolved in 2 ml of dimethylformamide and 188 mg (1.9 mmol) of 1,4,5,6-tetrahydro-pyrimidin-2-ylamine was added. The solution was stirred at room temperature for 16 hours. The solvent was removed in vacuo, the residue was dissolved in dichloromethane and the solution was washed twice with 10% aqueous citric acid solution and twice with water. Product in the combined aqueous phase was extracted five times with dichloromethane. The combined organic phase was dried with sodium sulfate, filtered and the solvent was removed in vacuo. The residue was chromatographed on silica gel eluting with dichloromethane/methanol (10/1), followed by DCM/AcOH/water (85:15:1.5:1.5). Yield: 70.6 mg.

MS (ES$^+$): m/e=580 (M+H$^+$).

1d) (2S)-2-Benzyloxycarbonylamino-3-{9-[3-(1,4,5,6-tetrahydro-pyrimidin-2-ylcarbamoyl)-propyl]-9H-purin-6-ylamino}-propionic acid 70 mg (Q.12 mmol) of (2S)-2-benzyloxycarbonylamino-3-{9-[3-(1,4,5,6-tetrahydro-pyrimidin-2-ylcarbamoyl)-propyl]-9H-purin-6-ylamino}-propionic acid tert-butyl ester was dissolved in 3 ml of trifluoroacetic acid/water (95/5). The solution was stirred at room temperature for 3 hours. The solvent was removed in vacuo and toluene was added to the residue and then removed in vacuo. The residue was dissolved in acetonitrile/water 1/1 and lyophilized. Yield: 51 mg (trifluoroacetate salt).

MS (ES$^+$): m/e=524 (M+H$^+$).

Example 2

(2S)-2-Benzyloxycarbonylamino-3-{2-methyl-7-[3-(1,4,5,6-tetrahydro-pyrimidin-2-ylcarbamoyl)-propyl]-7H-pyrrolo[2,3-d]pyrimidin-4-ylamino}-propionic acid

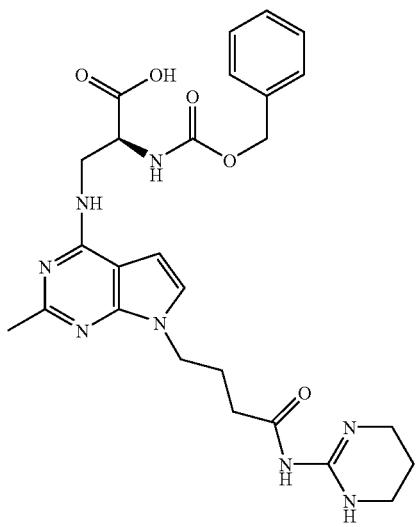

2a) 4-(4-Chloro-2-methyl-pyrrolo[2,3-d]pyrimidin-7-yl)-butyric acid ethyl ester 0.5 g (3 mmol) of 4-chloro-2-methyl-7H-pyrrolo[2,3-d]pyrimidine (prepared according to West and Beauchamp, J. Org. Chem. 26 (1961) 3809) was dissolved in 3 ml DMF and 2.06 g (15 mmol) of potassium carbonate was added to this solution. 0.431 ml (3 mmol) of 4-bromobutyric acid ethyl ester was added and the mixture was stirred at 50° C. for 45 minutes. The reaction mixture was diluted with 50 ml EE and washed three times with water, dried over MgSO$_4$, filtered and the solvent was removed in vacuo. Yield: 0.8 g.

MS (ES$^+$): m/e=282.1 (M+H+, 100%); 284.1 (30%).

2b) 4-[4-((2S)-2-Benzyloxycarbonylamino-2-tert-butoxycarbonyl-ethylamino)-2-methyl-pyrrolo[2,3-d]pyrimidin-7-yl]-butyric acid ethyl ester To a solution of 1000 mg (3.5 mmol) of 4-(4-chloro-2-methyl-pyrrolo[2,3-d]pyrimidin-7-yl)-butyric acid ethyl ester (example 2a) in 7 ml N-methylpyrrolidone were added 1590 mg (5.4 mmol) of (2S)-3-amino-2-benzyloxycarbonylamino-propionic acid tert-butyl ester and 5.9 ml triethylamine and the reaction was stirred at 100° C. for 36 h. The reaction was diluted with 85 ml EE and extracted with water, aqueous citric acid and again with water. The organic phase was dried over MgSO$_4$ filtered and the solvent was removed in vacuo. The residue was chromatographed on silica gel eluting with DCM/EE (2:1). Yield: 719 mg.

MS (ES$^+$): m/e=540.3 (M+H+, 100%).

2c) (2S)-2-Benzyloxycarbonylamino-3-{2-methyl-7-[3-(1,4,5,6-tetrahydro-pyrimidin-2-ylcarbamoyl)-propyl]-7H-pyrrolo[2,3-d]pyrimidin-4-ylamino}-propionic acid To a solution of 300 mg (0.5 mmol) of 4-[4-((2S)-2-benzyloxycarbonylamino-2-tert-butoxycarbonyl-ethylamino)-2-methyl-pyrrolo[2,3-d]pyrimidin-7-yl]-butyric acid ethyl ester (example 2b) in 5 ml of absol. THF were added 124 mg (1.82 mmol) of sodium ethanolate and 155 mg (1.56 mmol) of 1,4,5,6-tetrahydro-2-aminopyrimidine and the solution was stirred at room temperature for 6 hours. The mixture was brought to pH 7.0 and the solvent was removed in vacuo. The residue was chromatographed on silica gel eluting with DCM/MeOH/AcOH/$H_2O$ (90:10:1:1). Yield: 28 mg.

MS (ES+): m/e=537.2 (M+H+, 20%); 403.7 (40%); 269.1 (50%); 91 (100%).

Example 3

(2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(naphthalene-1-sulfonylamino)-propionic acid

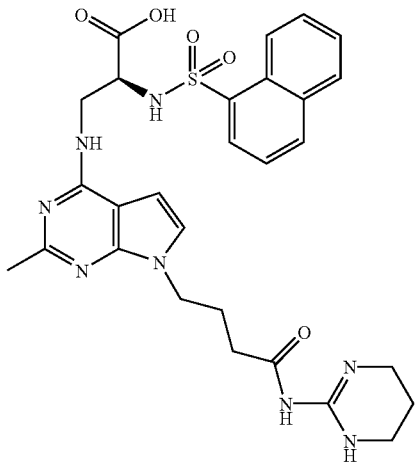

3a) 4-[4-((2S)-2-Amino-2-tert-butoxycarbonyl-ethylamino)-2-methyl-pyrrolo[2,3-d]pyrimidin-7-yl]-butyric acid ethyl ester 709 mg of 4-[4-((2S)-2-benzyloxycarbonylamino-2-tert-butoxycarbonyl-ethylamino)-2-methyl-pyrrolo[2,3-d]pyrimidin-7-yl]-butyric acid ethyl ester were dissolved in 40 ml of ethanol and 1 ml of acetic acid and were hydrogenated over 100 mg of Pd/C (10%) during 4 h at room temperature. The catalyst was removed by filtration, the solvent was removed in vacuo. The residue was dissolved in 60 ml of DCM and stirred with 10 ml of brine and additional 5 g of $NaHCO_3$. The phases were separated, the aqueous phase was extracted with DCM, the combined organic phases were dried over $MgSO_4$, filtered and the solvent was removed in vacuo. Yield: 475 mg.

3b) 4-{4-[(2S)-2-tert-Butoxycarbonyl-2-(naphthalene-1-sulfonylamino)-ethylamino]-2-methyl-pyrrolo[2,3-d]pyrimidin-7-yl}-butyric acid ethyl ester To a solution of 132 mg of 1-naphthalenesulfonic acid chloride (0.59 mmol) in 5 ml of absol. THF were added at −15° C. 158 mg (0.39 mmol) of 4-[4-((2S)-2-amino-2-tert-butoxycarbonyl-ethylamino)-2-methyl-pyrrolo[2,3-d]pyrimidin-7-yl]-butyric acid ethyl ester (example 3a) and 0.1 ml of DIPEA. The reaction mixture was stirred for 90 minutes at −5° C., then for 4.5 hours at room temperature. The DMF was removed in vacuo, the residue was taken up in DCM and washed with brine. The organic phase was dried over $MgSO_4$, filtered and the solvent was removed in vacuo. The residue was chromatographed on silica gel eluting with DCM/MeOH/AcOH/$H_2O$ (94:6:0.6:0.6). Yield: 138 mg.

Rf: 0.8 (DCM/MeOH/AcOH/$H_2O$, 90:10:1:1). MS (ES+): 596.3 (M+H$^{30}$, 100%).

3c) (2S)-3-(2-Methyl-7-[3-(1,4,5,6-tetrahydro-pyrimidin-2-ylcarbamoyl)-propyl]-7H-pyrrolo[2,3-d]pyrimidin-4-ylamino)-2-(naphthalene-1-sulfonylamino)-propionic acid tert-butyl ester To a solution of 128 mg (0.215 mmol) of 4-{4-[(2S)-2-tert-butoxycarbonyl-2-(naphthalene-1-sulfonylamino)-ethylamino]-2-methyl-pyrrolo[2,3-d]pyrimidin-7-yl}-butyric acid ethyl ester (example 3b) in 1 ml of DMF was added 105 mg (1.05 mmol) of 1,4,5,6-tetrahydro-pyrimidin-2-ylamine and the reaction mixture was stirred at room temperature for 4.5 hours. The solvent was removed in vacuo and the residue was taken up in DCM and washed with a saturated NaCl solution. The organic phase was dried over $MgSO_4$, filtered and the solvent was removed in vacuo. The residue was chromatographed on silica gel eluting with DCM/MeOH/AcOH/$H_2O$ (95:5:0.5:0.5). Yield: 72 mg.

MS (ES+): 649.3 (M+H$^{30}$, 100%).

3d) (2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(naphthalene-1-sulfonylamino)-propionic acid 1.5 ml of TFA were added to a solution of 75 mg of (2S)-3-(2-methyl-7-[3-(1,4,5,6-tetrahydro-pyrimidin-2-ylcarbamoyl)-propyl]-7H-pyrrolo[2,3-d]pyrimidin-4-ylamino)-2-(naphthalene-1-sulfonylamino)-propionic acid tert-butyl ester (example 3c) in 5 ml of DCM and stirred for 2 h at room temperature. Solvent and TFA were removed in vacuo, the residue was lyophilized from AcOH/$H_2O$ (1:1). Yield: 84 mg.

MS (ES+): 593.2 (M+H+, 90%); 297.2 (100).

Example 4

(2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(benzenesulfonylamino)-propionic acid

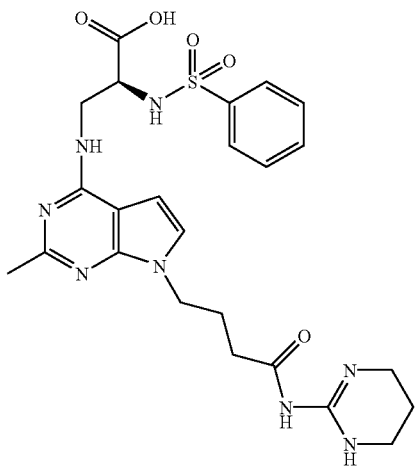

4a) 4-{4-[(2S)-2-tert-Butoxycarbonyl-2-(benzenesulfonylamino)-ethylamino]-2-methyl-pyrrolo[2,3-d]pyrimidin-7-yl}-butyric acid ethyl ester To a solution of 103.5 mg of benzenesulfonic acid chloride (0.59 mmol) were added at −15° C. 158 mg (0.39 mmol) of 4-[4-((2S)-2-amino-2-tert-butoxycarbonyl-ethylamino)-2-methyl-pyrrolo[2,3-d]pyrimidin-7-yl]-butyric acid ethyl ester (example 3a) and 0.1 ml DIPEA. The reaction mixture was stirred for 90 minutes at −5° C., then for 4.5 hours at room temperature. The DMF was removed in vacuo, the residue was taken up in DCM and washed with brine. The organic phase was dried over MgSO$_4$, filtered and the solvent was removed in vacuo. The residue was chromatographed on silica gel eluting with DCM/MeOH/AcOH/H$_2$O (94:6:0.6:0.6). Yield: 114 mg.

Rf: 0.7 (DCM/MeOH/AcOH/H$_2$O, 90:10:1:1). MS (ES+): 546.2 (M+H$^+$, 100%).

4b) (2S)-3-(2-Methyl-7-[3-(1,4,5,6-tetrahydro-pyrimidin-2-ylcarbamoyl)-propyl]-7H-pyrrolo[2,3-d]pyrimidin-4-ylamino)-2-(benzenesulfonylamino)-propionic acid tert-butyl ester To a solution of 104 mg (0.19 mmol) of 4-{4-[(2S)-2-tert-butoxycarbonyl-2-(benzenesulfonylamino)-ethylamino]-2-methyl-pyrrolo[2,3-d]pyrimidin-7-yl}-butyric acid ethyl ester (example 4a) in 1 ml of DMF was aded 100 mg (1.0 mmol) of 1,4,5,6-tetrahydro-pyrimidin-2-ylamine and the reaction mixture was stirred at room temperature for 4.5 hours. The solvent was removed in vacuo the residue was taken up in DCM and washed with a saturated NaCl solution. The organic phase was dried over MgSO$_4$, filtered and the solvent was removed in vacuo. The residue was chromatographed on silica gel eluting with DCM/MeOH/AcOH/H$_2$O (95:5:0.5:0.5). Yield: 70 mg.

MS (ES+): 699.3 (M+H$^+$, 100%).

4c) (2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(benzenesulfonylamino)-propionic Acid 1.5 ml of TFA were added to a solution of 70 mg of (2S)-3-(2-methyl-7-[3-(1,4,5,6-tetrahydro-pyrimidin-2-ylcarbamoyl)-propyl]-7H-pyrrolo[2,3-d]pyrimidin-4-ylamino)-2-(benzenesulfonylamino)-propionic acid tert-butyl ester (example 4b) in 5 ml DCM and stirred for 2 h at room temperature. Solvent and TFA were removed in vacuo, the residue was lyophilized from AcOH/H$_2$O (1:1). Yield: 71 mg.

MS (ES+): 543.2 (M+H$^+$, 50%); 272.1 (100).

Example 5

(2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(4-bromobenzenesulfonylamino)-propionic acid

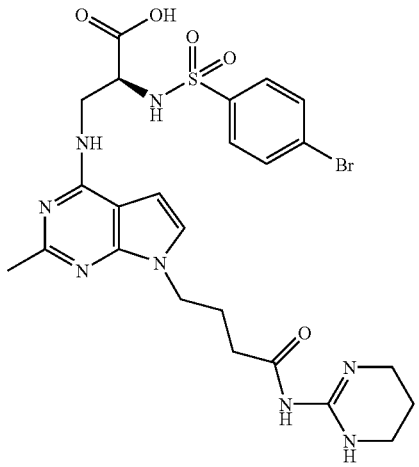

5a) 4-{4-[(2S)-2-tert-Butoxycarbonyl-2-(4-bromobenzenesulfonylamino)-ethylamino]-2-methyl-pyrrolo[2,3-d]pyrimidin-7-yl}-butyric acid ethyl ester To a solution of 149.5 mg of 4-bromobenzenesulfonic acid chloride (0.59 mmol) were added at −15° C. 158 mg (0.39 mmol) of 4-[4-((2S)-2-amino-2-tert-butoxycarbonyl-ethylamino)-2-methyl-pyrrolo[2,3-d]pyrimidin-7-yl]-butyric acid ethyl ester (example 3a) and 0.1 ml of DIPEA. The reaction was stirred for 90 minutes at −5° C., then for 4.5 hours at room temperature. The DMF was removed in vacuo, the residue was taken up in DCM and washed with brine. The organic phase was dried over MgSO$_4$, filtered and the solvent was removed in vacuo. The residue was chromatographed on silica gel eluting with DCM/MeOH/AcOH/H$_2$O (94:6:0.6:0.6). Yield: 126 mg.

Rf: 0.8 (DCM/MeOH/AcOH/H$_2$O, 90:10:1:1). MS (ES+): 624.1, 626.1 (M+H$^+$, 100%).

5b) (2S)-3-(2-Methyl-7-[3-(1,4,5,6-tetrahydro-pyrimidin-2-ylcarbamoyl)-propyl]-7H-pyrrolo[2,3-d]pyrimidin-4-ylamino)-2-(4-bromobenzenesulfonylamino)-propionic acid tert-butyl ester To a solution of 116 mg (0.19 mmol) of 4-{4-[(2S)-2-tert-butoxycarbonyl-2-(4-bromobenzenesulfonylamino)-ethylamino]-2-methyl-pyrrolo[2,3-d]pyrimidin-7-yl}-butyric acid ethyl ester (example 5a) in 1 ml of DMF was added 100 mg (1.0 mmol) of 1,4,5,6-tetrahydro-pyrinmidin-2-ylamine and the reaction mixture was stirred at room temperature for 4.5 hours. The solvent was removed in vacuo the residue was taken up in DCM and washed with a saturated NaCl solution. The organic phase was dried over MgSO$_4$, filtered and the solvent was removed in vacuo. The residue was chromatographed on silica gel eluting with DCM/MeOH/AcOH/H$_2$O (95:5:0.5:0.5). Yield: 70 mg.

MS (ES+): 677.2; 679.2 (M+H$^+$, 100%).

5c) (2S)-3-{2-Methyl-7-[3-(1,4,5,6-tetrahydro-pyrimidin-2-ylcarbamoyl)-propyl]-7H-pyrrolo[2,3-d]pyrimidin-4-ylamino}-2-(4-bromobenzenesulfonylamino)-propionic acid 1.5 ml of TFA were added to a solution of 70 mg of (2S)-3-(2-methyl-7-[3-(1,4,5,6-tetrahydro-pyrimidin-2-yl-carbamoyl)-propyl]-7H-pyrrolo[2,3-d]pyrimidin-4-ylamino)-2-(4-bromobenzenesulfonylamino)-propionic acid tert-butyl ester (example 5b) in 5 ml of DCM and stirred for 2 h at room temperature. Solvent and TFA were removed in vacuo, the residue was lyophilized from AcOH/H$_2$O (1:1). Yield: 76 mg.

MS (ES+): 621.0, 623.0 (M+H$^+$, 40%); 311.1, 312.0 (100).

Example 6

(2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(4-bromobenzenesulfonylamino)-propionic acid

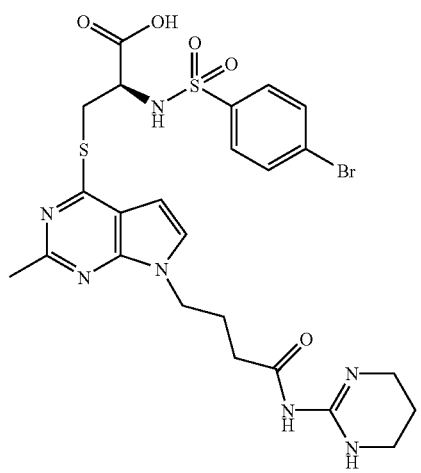

6a) N,N'-bis-(4-Bromobenzenesulfonyl)-(R)-cystine-bis-tert-butyl ester

To a suspension of 1 g (2.35 mmol) of (R)-cystine-bis-tert-butylester in 12 ml of THF were added at 0° C. 1.2 g (4.7 mmol) of 4-bromobenzenesulfonic acid chloride and 1.64 ml of TEA. The reaction mixture was brought to room temperature and stirred for 2 h. The mixture was poured on 100 ml ice-water and brought to pH 2.5 with citric acid. After 30 minutes, the oily product crystallized and was filtered off, washed with water and dried. Yield: 1.6 g.

MS(ES+): 788.9, 790.9, 792.9 (M+H$^+$, 30%); 732.9, 734.9, 736.9 (50); 676.8, 678.8, 680.8 (100).

6b) N-(4-Bromobenzenesulfonyl)-(R)-cysteine-tert-butyl ester

To a solution of 760 mg (0.96 mmol) of N,N'-bis-(4-bromobenzenesulfonyl)-(R)-cystine-bis-tert-butyl ester (example 6a) in 2 ml of DCM were added 631 mg (4.07 mmol) of dithioerythritol (DTE) and 0.4 ml of TEA and the mixture was stirred at room temperature for 1.5 hours. The solution was diluted with 30 ml of DCM and extracted with 10% citric acid and with water. The solvent was evaporated and the product was used directly in the next reaction.

6c) 4-{4-[(2R)-2-(4-Bromobenzenesulfonylamino)-2-tert-butoxycarbonyl-ethylsulfanyl]-2-methyl-pyrrolo[2,3-d]pyrimidin-7-yl}-butyric acid ethyl ester 279 mg of 4-(4-chloro-2-methyl-pyrrolo[2,3-d]pyrimidin-7-yl)-butyric acid ethyl ester (example 2a) and 655 mg of N-(4-bromobenzenesulfonyl)-(R)-cysteine-tert-butyl ester (example 6b) were dissolved in 2 ml of NMP and 0.68 ml of DIPEA were added. The reaction mixture was heated to 100° C. for 4 h. The mixture was diluted with 60 ml of EE and extracted with 10% citric acid, saturated NaCl solution and with water. The organic phase was dried over MgSO$_4$ and the solvent was removed in vacuo. The crude product was chromatographed on silica gel eluting with EE/toluene (1:6). Yield: 108 mg.

MS (ES+): 641.1, 643.1 (M+H$^{30}$, 100%).

6d) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(4-bromobenzenesulfonylamino)-propionic acid tert-butyl ester Preparation in analogy to example 5b from 4-{4-[(2R)-2-(4-bromobenzenesulfonylamino)-2-tert-butoxycarbonyl-ethylsulfanyl]-2-methyl-pyrrolo[2,3-d]pyrimidin-7-yl}-butyric acid ethyl ester. Yield: 15%.

MS (ES+): 694.2, 696.2 (M+H$^+$, 100%).

6e) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(4-bromobenzenesulfonylamino)-propionic acid Preparation in analogy to example 5c from (2R)-3-{2-methyl-7-[3-(1,4,5,6-tetrahydro-pyrimidin-2-ylcarbamoyl)-propyl]-7H-pyrrolo[2,3-d]pyrimidin-4-ylsulfanyl}-2-(4-bromobenzenesulfonylamino)-propionic acid tert-butyl ester (example 6d). Yield: 100%.

MS (ES+): 638.0, 640.0 (M+H$^+$, 20%).

Example 7

(2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(naphthalene-1-sulfonylamino)-propionic acid

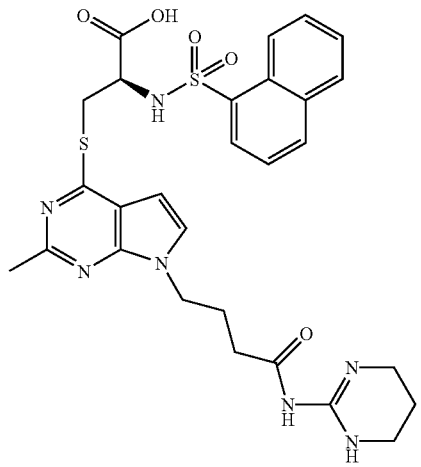

7a) N,N'-bis-(Naphthalene-1-sulfonyl)-(R)-cystine-bis-tert-butyl ester

Preparation in analogy to example 6a from 1 g (2.35 mmol) of (R)-cystine-bis-tert-butylester and 1.32 g (5.8 mmol) of 1-naphthalenesulfonic acid chloride. Yield: 1.78 g (oily crystals).
MS(ES+): 733.1 (M+H$^+$, 20%); 677.1 (50); 621.0 (100).

7b) N-(Naphthalene-1-sulfonyl)-(R)-cysteine-tert-butyl ester

Preparation in analogy to example 6b from 890 mg of N,N'-bis-(naphthalene-1-sulfonyl)-(R)-cystine-bis-tert-butyl ester (example 7a). Yield: 820 mg, used directly in the next reaction.

7c) 4-{4-[(2R)-2-(Naphthalene-1-sulfonylamino)-2-tert-butoxycarbonyl-ethylsulfanyl]-2-methyl-pyrrolo[2,3-d]pyrimidin-7-yl}-butyric acid ethyl ester Preparation in analogy to example 6c from 282 mg of 4-(4-chloro-2-methyl-pyrrolo[2,3-d]pyrimidin-7-yl)-butyric acid ethyl ester (example 2a) and 440 mg of N-(naphthalene-1-sulfonyl)-(R)-cysteine-tert-butyl ester. Yield: 110 mg.
MS (ES+): 613.2 (M+H$^+$, 100%).

7d) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(naphthalene-1-sulfonylamino)-propionic acid tert-butyl ester Preparation in analogy to example 5b from 4-{4-[(2R)-2-(naphthalene-1-sulfonylamino)-2-tert-butoxycarbonyl-ethylsulfanyl]-2-methyl-pyrrolo[2,3-d]pyrimidin-7-yl}-butyric acid ethyl ester (example 7c). Yield: 12%.
MS (ES+): 666.2 (M+H$^+$, 100%).

7e) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(naphthalene-1-sulfonylamino)-propionic acid Preparation in analogy to example 5c from (2R)-3-{2-methyl-7-[3-(1,4,5,6-tetrahydro-pyrimidin-2-ylcarbamoyl)-propyl]-7H-pyrrolo[2,3-d]pyrimidin-4-ylsulfanyl}-2-(naphthalene-1-sulfonylamino)-propionic acid tert-butyl ester (example 7d). Yield: 92%.
MS (ES+): 610.2 (M+H$^+$, 20%).

Example 8

(2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(benzenesulfonylamino)-propionic acid

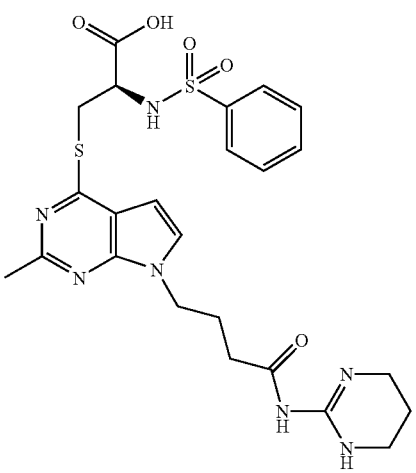

8a) N,N-bis-(Benzenesulfonyl)-cystine-bis-tert-butyl ester

Preparation in analogy to example 6a from 1 g (2.35 mmol) of (R)-cystine-bis-tert-butylester and 0.83 g (4.7 mmol) benzenesulfonic acid chloride. Yield: 1.5 g.
MS(ES+): 633.1 (M+H$^+$, 20%); 577.1 (50); 521.0 (100).

8b) N-(Benzenesulfonyl)-(R)-cysteine-tert-butyl ester

Preparation in analogy to example 6b from 710 mg of N,N'-bis-(benzenesulfonyl)-(R)-cystine-bis-tert-butyl ester (example 8a). Yield: 655 mg, used directly in the subsequent reaction step.

8c) 4-{4-[(2R)-2-(Benzenesulfonylamino)-2-tert-butoxycarbonyl-ethylsulfanyl]-2-methyl-pyrrolo[2,3-d]pyrimidin-7-yl}-butyric acid ethyl ester Preparation in analogy to example 6c from 282 mg of 4-(4-chloro-2-methyl-pyrrolo[2,3-d]pyrimidin-7-yl)-butyric acid ethyl ester (example 2a) and 475 mg of N-(benzenesulfonylamino)-(R)-cysteine-tert-butyl ester (example 8b). Yield: 112 mg.
MS (ES+): 563.2 (M+H$^+$, 100%).

8d) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulany}-2-(benzenesulfonylamino)-propionic acid tert-butyl ester Preparation in analogy to example 5b from 4-{4-[(2R)-2-(benzenesulfonylamino)-2-tert-butoxycarbonyl-ethylsulfanyl]-2-methyl-pyrrolo[2,3-d]pyrimidin-7-yl}-butyric acid ethyl ester (example 8c). Yield: 8%.

8e) (2R)-3-{2-Methyl-7-[3-(1,4,5,6-tetrahydro-pyrimidin-2-ylcarbamoyl)-propyl]-7H-pyrrolo[2,3-d]pyrimidin-4-ylsulfanyl}-2-(benzenesulfonylamino)-propionic acid Preparation in analogy to example 5c from 10 mg of (2R)-3-{2-methyl-7-[3-(1,4,5,6-tetrahydro-pyrimidin-2-ylcarbamoyl)-propyl]-7H-pyrrolo[2,3-d]pyrimidin-4-ylsulfanyl}-2-(benzenesulfonylamino)-propionic acid tert-butyl ester (example 8d). Yield: 5.5 mg.
MS (ES+): 560.1 (M+H$^+$, 45%).

Pharmacological Testing

Kistrin Binding Assay

The inhibition of the binding of kistrin to human vitronectin receptor (VnR) described below is a test method by which the antagonistic action of the compounds of the invention on the vitronectin receptor $\alpha_v\beta_3$ can be determined ($\alpha_v\beta_3$ ELISA Test; the test method is abbreviated as "K/VnR" in the listing of the test results).

Purification of Kistrin

Kistrin was purified according to the methods of Dennis et al., as described in Proc. Natl. Acad. Sci. USA 87 (1989) 2471 and Proteins: Structure, Function and Genetics 15 (1993)312.

Purification of Human vitronectin Receptor ($\alpha_v\beta_3$)

Human vitronectin receptor was obtained from the human placenta according to the method of Pytela et al., Methods Enzymol. 144 (1987) 475. Human vitronectin receptor $\alpha_v\beta_3$ can also be obtained from some cell lines (for example from 293 cells, a human embryonic kidney cell line) which are co-transfected with DNA sequences for both subunits $\alpha_v$ and $\beta_3$ of the vitronectin receptor. The subunits are extracted with octyl glycoside and then chromatographed through concanavalin A, heparin-Sepharose and S-300.

Monoclonal Antibodies

Murine monoclonal antibodies which are specific for the $\beta_3$ subunits of the vitronectin receptor, were prepared according to the method of Newman et al., Blood, 1985, 227, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates were coated with a solution of kistrin (0.002 mg/ml) according to the method of Dennis et al., as described in Proteins: Structure, Function and Genetics 15 (1993) 312. The plates were then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), MgCl$_2$ (1 mM), CaCl$_2$ (1 mM), MnCl$_2$ (1 mM), pH 7). Solutions of known inhibitors and of the test substances were prepared in concentrations from $2\times10^{-12}$ to $2\times10^{-6}$ mol/l in assay buffer (BSA (0.5%), RIA grade or better); Tris-HCl (50 mM), NaCl (100 mM), MgCl$_2$ (1 mM), CaCl$_2$ (1 mM), MnCl$_2$ (1 mM), pH 7). The blocked plates were emptied, and in each case 0.025 ml of this solution which contains a defined concentration ($2\times10^{-12}$ to $2\times10^{-6}$ mol/l) either of a known inhibitor or of a test substance, were added to each well. 0.025 ml of a solution of the vitronectin receptor in assay buffer (0.03 mg/ml) was pipetted into each well of the plate and the plate was incubated at room temperature for 60-180 min on a shaker. In the meantime, a solution (6 ml/plate) of a murine monoclonal antibody specific for the P3 subunit of the vitronectin receptor was prepared in assay buffer (0.0015 mg/ml). A second rabbit antibody (0.001 ml of stock solution/6 ml of the murine monoclonal anti-$\beta_3$ antibody solution) which is an anti-mouse Fc HRP antibody conjugate was added to this solution, and this mixture of murine anti-$\beta_3$ antibody and rabbit anti-mouse Fc HRP antibody conjugate was incubated during the time of the receptor-inhibitor incubation. The test plates were washed four times with PBS solution which contains 0.05% Tween-20, and in each case 0.05 ml/well of the antibody mixture was pipefted into each well of the plate and incubated for 60-180 min. The plate was washed four times with PBS/0.05% Tween-20 and then developed with 0.05 ml/well of a PBS solution which contained 0.67 mg/ml of ophenylenediamine and 0.012% of H$_2$O$_2$. Alternatively to this, o-phenylenediamine can be employed in a buffer (pH 5) which contains Na$_3$PO$_4$ and citric acid. The color development was stopped using 1 N H$_2$SO$_4$ (0.05 ml/well). The absorption for each well was measured at 492-405 nm and the data are evaluated by standard methods.

The following test results (inhibitory concentrations IC$_{50}$) were obtained.

| | K/VnR IC$_{50}$ [nM] |
|---|---|
| Example 1 | 22.0 |
| Example 2 | 3.5 |
| Example 3 | 2.2 |
| Example 4 | 3.0 |
| Example 5 | 2.6 |
| Example 6 | 13.5 |
| Example 7 | 5.0 |
| Example 8 | 10.0 |

The invention claimed is:
1. A compound of the formula

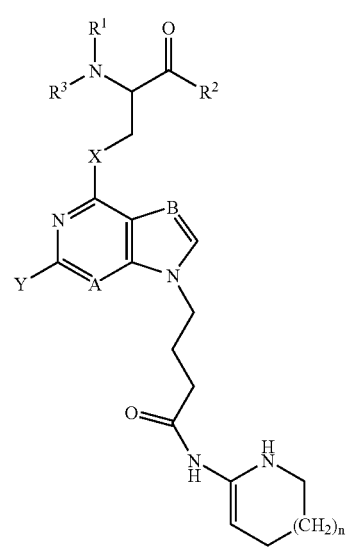

wherein
n is zero or one or two;
A is nitrogen or CH;
B is nitrogen or CH;
X is selected from the group consisting of $-NR^1-$, $-O-$ and $-S-$;
Y is selected from the group consisting of hydrogen, halogen, $NR^6R^{6'}$, $(C_1-C_{18})$-alkyl, $(C_3-C_{14})$-cycloalkyl-$(C_1-C_8)$-alkyl, $(C_3-C_{14})$-cycloalkyl, $(C_5-C_{14})$-aryl-$(C_1-C_8)$-alkyl, $(C_5-C_{14})$-aryl, $(C_5-C_{14})$-heteroaryl and $(C_5-C_{14})$-heteroaryl-$(C_1-C_8)$-alkyl where aryl, heteroaryl, cycloalkyl and alkyl can be substituted one, two or three times with at least one member selected from the group consisting of fluorine, chlorine, bromine, cyano, $-CF_3$, hydroxy, nitro, carboxyl, $(C_1-C_8)$-alkyl, $(C_1-C_6)$-alkoxy, $(C_1-C_6)$-alkoxy-$(C_1-C_6)$-alkyl, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_8)$-alkylcarbonyl, $(C_1-C_6)$-alkanoylamino, $(C_5-C_{14})$-arylsulfonylamino, $(C_5-C_{14})$-aryl-$(C_1-C_8)$-alkylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_5-C_{14})$-aryl-$(C_1-C_8)$-alkylaminosulfonyl, $(C_5-C_{14})$-heteroaryl-$(C_1-C_8)$-alkylaminosulfonyl, $(C_5-C_{14})$-aryl-$(C_1-C_8)$-alkylsulfonyl, $(C_5-C_{14})$-heteroaryl-$(C_1-C_8)$-alkylsulfonyl, $(C_5-C_{14})$-aryl, and $(C_5-C_{14})$-heteroaryl;
$R^1$ is hydrogen or $(C_1-C_4)$-alkyl;
$R^2$ is selected from the group consisting of hydroxy, amino, $(C_1-C_6)$-alkyl-CO-O-$(C_1-C_4)$-alkoxy, $(C_1-C_6)$-alkoxy, $(C_3-C_{16})$-cycloalkyloxy, $(C_3-C_{16})$-cycloalkyl-CO-O-$(C_1-C_4)$-alkoxy, and $(C_5-C_{14})$-aryl-CO-O-$(C_1-C_4)$-alkoxy where aryl, alkyl, alkoxy, cycloalkyloxy and cycloalkyl are unsubstituted or substituted by one, two or three members selected from the group consisting of hydroxyl, halogen, oxo, $-CN$, $(C_1-C_4)$-alkyl-CO, $(C_1-C_4)$-alkyl-CO-NH, $(C_1-C_4)$-alkyl-NH-CO-, COOH, $(C_1-C_4)$-alkyl, $(C_1-C_4)$-alkoxy, $(C_1-C_4)$-alkyl-S(O)$_2$ and $-NR^6R^{6'}$, or $R^2$ is an amino acid, bonded to C=O through its amino group;
$R^3$ is selected from the group consisting of $-R^4$, $-R^4C(O)R^5$, $-R^4OC(O)R^5$, $-R^4S(O)_2R^5$, $-R^4N(R^1)C(O)R^5$, $-R^4N(R^1)S(O)_2R^5$;
$R^4$ is selected from the group consisting of $(C_1-C_{18})$-alkyl, $(C_3-C_{14})$-cycloalkyl-$(C_1-C_8)$-alkyl, $(C_3-C_{14})$-cycloalkyl, $(C_5-C_{14})$-aryl-$(C_1-C_8)$-alkyl, $(C_5-C_{14})$-aryl, $(C_5-C_{14})$-heteroaryl and $(C_5-C_{14})$-heteroaryl-$(C_1-C_8)$-alkyl where aryl, heteroaryl, cycloalkyl and alkyl can be substituted one, two or three times with a member selected from the group consisting of fluorine, chlorine, bromine, cyano, $-CF_3$, nitro, hydroxy, carboxyl, $(C_1-C_8)$-alkyl, $(C_1-C_6)$-alkoxy, $(C_1-C_6)$-alkoxy-$(C_1-C_6)$-alkyl, $(C_1-C_6)$-alkoxycarbonyl, $(C_1-C_6)$-alkylcarbonyl, $(C_1-C_6)$-alkylaminocarbonyl, $(C_1-C_6)$-alkoxy-$(C_1-C_6)$-alkoxy-, $(C_5-C_{14})$-aryl-$(C_1-C_8)$-alkylcarbonyl, $(C_1-C_6)$-alkanoylamino, $(C_5-C_{14})$-arylsulfonylamino, $(C_1-C_6)$-alkylsulfonylamino, $(C_1-C_6)$-alkylamino, di-$((C_1-C_6)$-alkyl)amino, $(C_1-C_6)$-alkylsulfonyl, $(C_1-C_6)$-alkylaminosulfonyl, $(C_5-C_{14})$-aryl-$(C_1-C_8)$-alkylaminosulfonyl, $(C_5-C_{14})$-aryl-$(C_1-C_8)$-alkylsulfonyl, $(C_5-C_{14})$-aryl, and $(C_5-C_{14})$-heteroaryl;
$R^5$ is $(C_1-C_4)$-alkylene or a direct bond;
$R^6$ and $R^{6'}$ are independently from the group consisting of hydrogen, $(C_1-C_8)$-alkyl, $(C_3-C_8)$-cycloalkyl, $(C_3-C_{14})$-cycloalkyl-$(C_1-C_8)$-alkyl, $(C_5-C_{14})$-aryl, $(C_5-C_{14})$-aryl-$(C_1-C_8)$-alkyl, where in the aryl moiety, one, two three, four or five ring carbon atoms can be replaced by heteroatoms selected from the group consisting of N, O, S, or $R^6$ and $R^{6'}$, together with the atom connecting them, form a ring system;
in all its stereoisomeric forms and mixtures thereof, and its physiologically tolerable salts.

2. A compound of claim 1, wherein
n is zero or one or two;
X is $-NR^1-$ or $-S-$;
Y is selected from the group consisting of hydrogen, $(C_1-C_6)$-alkyl, $(C_5-C_7)$-cycloalkyl-$(C_1-C_3)$-alkyl, $(C_5-C_7)$-cycloalkyl, $(C_5-C_{14})$-aryl-$(C_1-C_3)$-alkyl, $(C_5-C_{14})$-aryl, $(C_5-C_{14})$-heteroaryl and $(C_5-C_{14})$-heteroaryl-$(C_1-C_3)$-alkyl and $(C_5-C_{14})$-heteroaryl-$(C_0-C_3)$-alkyl in which aryl, heteroaryl, cycloalkyl and alkyl can be substituted one, two or three times with a member selected from the group consisting of fluorine, chlorine, bromine, hydroxy, cyano, $-CF_3$, nitro, $(C_1-C_4)$-alkyl, $(C_5-C_{14})$-aryl, and $(C_5-C_{14})$-heteroaryl;
$R^1$ is hydrogen or methyl;
$R^2$ is selected from the group consisting of hydroxy, animo, $(C_1-C_6)$-alkyl-CO-O-$(C_1-C_4)$-alkoxy, $(C_1-C_6)$-alkoxy;
$R^3$ is selected from the group consisting of $-R^4$, $-R^4C(O)R^5$, $-R^4OC(O)R^5$, $-R^4S(O)_2R^5$, $-R^4N(R^1)C(O)R^5$, and $-R^4N(R^1)S(O)_2R^5$;
$R^4$ is selected from the group consisting of $(C_1-C_{18})$-alkyl, $(C_3-C_{14})$-cycloalkyl-$(C_1-C_8)$-alkyl, $(C_3-C_{14})$-cycloalkyl, $(C_5-C_{14})$-aryl-$(C_1-C_8)$-alkyl, $(C_5-C_{14})$-aryl, $(C_5-C_{14})$-heteroaryl and $(C_5-C_{14})$-heteroaryl-$(C_1-C_8)$-alkyl in which aryl, heteroaryl, cycloalkyl and alkyl can be substituted one, two or three times with a member selected from the group consisting of fluorine, chlorine, bromine, hydroxy, cyano, $-CF_3$, $(C_1-C_4)$-alkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkylaminocarbonyl, $(C_1-C_4)$-alkylamino, di-$((C_1-C_4)$-alkyl)amino, $(C_1-C_4)$-alkylsulfonyl, $(C_1-C_4)$-alkylaminosulfonyl, $(C_5-C_{14})$-aryl-$(C_1-C_4)$-alkylaminosulfonyl, $(C_5-C_{14})$-aryl-$(C_1-C_4)$-alkylsulfonyl, $(C_5-C_{14})$-aryl and $(C_5-C_{14})$-heteroaryl;
$R^5$ is a direct bond;
in all its stereoisomeric forms and mixtures thereof, and its physiologically tolerable salts.

3. A compound of claim 1, wherein
n is zero or one;
X is $-NR^1-$ or $-S-$;
Y is selected from the group consisting of hydrogen, $(C_1-C_6)$-alkyl, and $(C_5-C_{14})$-aryl where aryl and alkyl can be substituted one or two times with a member selected from the group consisting of fluorine, chlorine, bromine, hydroxy, $-CF_3$, and $(C_1-C_4)$-alkyl;
$R^1$ is hydrogen or methyl;
$R^2$ is hydroxy or $(C_1-C_4)$-alkoxy;
$R^3$ is selected from the group consisting of $-R^4$, $-R^4OC(O)R^5$ and $R^4S(O)_2R^5$;
$R^4$ is selected from the group consisting of $(C_1-C_{10})$-alkyl, $(C_3-C_{14})$-cycloalkyl-$(C_1-C_8)$-alkyl, $(C_3-C_{14})$-cycloalkyl, $(C_5-C_{14})$-aryl-$(C_1-C_8)$-alkyl, $(C_5-C_{14})$-aryl, $(C_5-C_{14})$-heteroaryl and $(C_5-C_{14})$-heteroaryl-$(C_1-C_8)$-alkyl where aryl, heteroaryl, cycloalkyl and alkyl can be substituted one, two or three times with a member selected from the group consisting of fluorine, chlorine, bromine, hydroxy, $-CF_3$, $(C_1-C_4)$-alkyl, $(C_1-C_4)$-alkoxy, $(C_1-C_4)$-alkylcarbonyl, $(C_5-C_{14})$-aryl, $(C_5-C_{14})$-heteroaryl;

R$^5$ is a direct bond;

in all its stereoisomeric forms and mixtures thereof, and its physiologically tolerable salts.

4. A compound of claim 1, wherein n is one;

X is —NR$^1$— or —S—;

Y is hydrogen or (C$_1$-C$_3$)-alkyl;

R$^1$ is hydrogen;

R$^2$ is hydroxy or (C$_1$-C$_4$)-alkoxy;

R$^3$ is selected from the group consisting of —R$^4$, —R$^4$OC(O)R$^5$, R$^4$S(O)$_2$R$^5$;

R$^4$ is selected from the group consisting of (C$_1$-C$_{10}$)-alkyl, (C$_3$-C$_{14}$)-cycloalkyl-(C$_1$-C$_8$)-alkyl, (C$_3$-C$_{14}$)-cycloalkyl, (C$_5$-C$_{14}$)-aryl-(C$_1$-C$_8$)-alkyl, (C$_5$-C$_{14}$)-aryl, (C$_5$-C$_{14}$)-heteroaryl and (C$_5$-C$_{14}$)-heteroaryl-(C$_1$-C$_8$)-alkyl where aryl, heteroaryl, cycloalkyl and alkyl can be substituted one or two times with fluorine, chlorine, bromine, hydroxy, —CF$_3$, and (C$_1$-C$_4$)-alkyl;

R$^5$ is a direct bond;

in all its stereoisomeric forms and mixtures thereof, and its physiologically tolerable salts.

5. A compound of claim 1, wherein n is one;

X is —NR$^1$—;

Y is hydrogen or (C$_1$-C$_3$)-alkyl;

R$^1$ is hydrogen;

R$^2$ is hydroxy or (C$_1$-C$_4$)-alkoxy;

R$^3$ is —R$^4$OC(O)R$^5$, —R$^4$S(O)$_2$R$^5$;

R$^4$ is selected from the group consisting of (C$_1$-C$_{10}$)-alkyl, (C$_3$-C$_{14}$)-cycloalkyl-(C$_1$-C$_8$)-alkyl, (C$_3$-C$_{14}$)-cycloalkyl, (C$_5$-C$_{14}$)-aryl-(C$_1$-C$_8$)-alkyl, (C$_5$-C$_{14}$)-aryl, (C$_5$-C$_{14}$)-heteroaryl and (C$_5$-C$_{14}$)-heteroaryl-(C$_1$-C$_8$)-alkyl where aryl, heteroaryl, cycloalkyl and alkyl can be substituted one or two times with a member selected from the group consisting of fluorine, chlorine, bromine, hydroxy, —CF$_3$, and (C$_1$-C$_4$)-alkyl;

R$^5$ is a direct bond;

in all its stereoisomeric forms and mixtures thereof, and its physiologically tolerable salts.

6. A compound of claim 1, wherein n is one;

X is —S—;

Y is hydrogen or (C$_1$-C$_3$)-alkyl;

R$^1$ is hydrogen;

R$^2$ is hydroxy or (C$_1$-C$_4$)-alkoxy;

R$^3$ is selected from the group consisting of —R$^4$, —R$^4$OC(O)R$^5$, and —R$^4$S(O)$_2$R$^5$;

R$^4$ is selected from the group consisting of (C$_1$-C$_{10}$)-alkyl, (C$_3$-C$_{14}$)-cycloalkyl-(C$_1$-C$_8$)-alkyl, (C$_3$-C$_{14}$)-cycloalkyl, (C$_5$-C$_{14}$)-aryl-(C$_1$-C$_8$)-alkyl, (C$_5$-C$_{14}$)-aryl, (C$_5$-C$_{14}$)-heteroaryl and (C$_5$-C$_{14}$)-heteroaryl-(C$_1$-C$_8$)-alkyl where aryl, heteroaryl, cycloalkyl and alkyl can be substituted one or two times with a member selected from the group consisting of fluorine, chlorine, bromine, hydroxy, —CF$_3$, and (C$_1$-C$_4$)-alkyl;

R$^5$ is a direct bond;

in all its stereoisomeric forms and mixtures thereof, and its physiologically tolerable salts.

7. A process for the preparation of a compound of claim 1, comprising reacting a compound of the formula

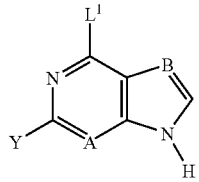

II wherein Y, A and B are defined as in claim 1 and L$^1$ is a nucleophilically substitutable leaving group, with a compound of the formula

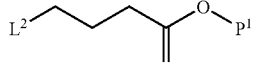

III wherein L$^2$ is a nucleophilically substitutable leaving group and P$^1$ is a carboxylic acid protecting group, to form a compound of the formula

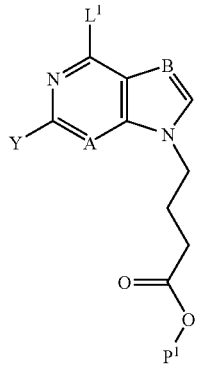

IV wherein Y, A, B, L$^1$ and P$^1$ are defined as above and reacting the compound formula IV with a compound of the formula

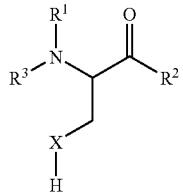

V wherein X, R$^1$, R$^2$ and R$^3$ are defined as in claim 1, to obtain a compound of the formula

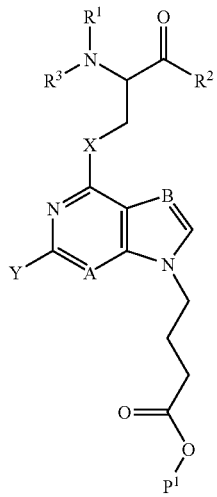

VI wherein $R^1$, $R^2$ and $R^3$, X, Y, A, B, $L^1$, $P^1$ are defined as above and, after removal of $P^1$, reacting the compound of formula VI with a compound of the formula

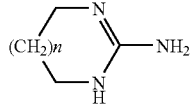 VIII wherein n is defined as in claim 1.

8. A composition for treating osteophorosis comprising an amount of a compound of claim 1 sufficient to treat osteoporosis and an inert pharmaceutical carrier.

9. A method of inhibiting cell adhesion and bone resorption by osteoclasts in warm-blooded animals comprising administering to warm-blooded animals in need thereof an amount of a compound of claim 1 sufficient to inhibit cell adhesion and bone resorption by osteoclasts.

* * * * *